United States Patent
Lecomte

(10) Patent No.: US 12,263,102 B2
(45) Date of Patent: Apr. 1, 2025

(54) PROSTHETIC FOOT WITH VARIABLE STIFFNESS ANKLE

(71) Applicant: Össur Iceland ehf, Reykjavik (IS)

(72) Inventor: Christophe Guy Lecomte, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 292 days.

(21) Appl. No.: 17/459,918

(22) Filed: Aug. 27, 2021

(65) Prior Publication Data
US 2022/0062009 A1    Mar. 3, 2022

Related U.S. Application Data

(60) Provisional application No. 63/071,604, filed on Aug. 28, 2020.

(51) Int. Cl.
| | | |
|---|---|---|
| *A61F 2/66* | (2006.01) | |
| *A61F 2/50* | (2006.01) | |
| *A61F 2/70* | (2006.01) | |

(52) U.S. Cl.
CPC .............. *A61F 2/6607* (2013.01); *A61F 2/70* (2013.01); *A61F 2002/503* (2013.01); *A61F 2002/6664* (2013.01); *A61F 2002/707* (2013.01)

(58) Field of Classification Search
CPC .... A61F 2/6607; A61F 2/70; A61F 2002/503; A61F 2002/6664; A61F 2002/707
See application file for complete search history.

(56) References Cited

U.S. PATENT DOCUMENTS

| | | |
|---|---|---|
| 4,636,220 A | 1/1987 | Ziegelmeyer |
| 5,112,356 A | 5/1992 | Harris et al. |
| 5,376,133 A | 12/1994 | Gramnaes |
| 5,387,246 A | 2/1995 | Phillips |
| 5,571,210 A | 11/1996 | Lindh |
| 5,701,686 A | 12/1997 | Herr et al. |
| 5,957,981 A | 9/1999 | Gramnaes |
| 6,099,572 A | 8/2000 | Mosler et al. |

(Continued)

FOREIGN PATENT DOCUMENTS

| | | |
|---|---|---|
| CA | 2 127 691 | 5/1994 |
| CA | 2 103 341 | 4/1995 |

(Continued)

OTHER PUBLICATIONS

Burden et al., "Numerical Analysis", Second Edition, Review of Calculus, Section 1.1, 1981, Prindle, Weber & Schmidt, p. 3.

(Continued)

*Primary Examiner* — Jerrah Edwards
*Assistant Examiner* — Maximilian Tobias Spencer
(74) *Attorney, Agent, or Firm* — Knobbe, Martens, Olson & Bear, LLP

(57) ABSTRACT

A prosthetic foot can have an ankle unit with semi-active adjustable stiffness. In one example, the adjustable stiffness is in the sagittal plane. The ankle stiffness can be varied by the ankle unit in response a user input, which can be received via a wireless communication device. The ankle unit can include two load application locations for one or more cantilever springs so as to provide different stiffness in plantarflexion and dorsiflexion. The positions of the two load application locations can be varied in order to vary the stiffness.

21 Claims, 31 Drawing Sheets

(56) References Cited

U.S. PATENT DOCUMENTS

| | | | |
|---|---|---|---|
| 6,202,806 B1 | 3/2001 | Sandrin | |
| 6,241,776 B1 | 6/2001 | Christensen | |
| 6,387,134 B1 | 5/2002 | Parker et al. | |
| 6,402,790 B1 | 6/2002 | Celebi | |
| 6,443,993 B1 | 9/2002 | Koniuk | |
| 6,562,075 B2 | 5/2003 | Townsend et al. | |
| 6,767,370 B1 | 7/2004 | Mosler et al. | |
| 6,942,704 B2 | 9/2005 | Sulprizio | |
| 7,029,500 B2 | 4/2006 | Martin | |
| 7,341,603 B2 | 3/2008 | Christensen | |
| 7,507,259 B2 | 3/2009 | Townsend et al. | |
| 7,578,852 B2 | 8/2009 | Townsend et al. | |
| 7,727,285 B2 | 6/2010 | Christensen et al. | |
| 7,763,082 B1 | 7/2010 | Curtis | |
| 7,766,974 B2 | 8/2010 | Curtis | |
| 7,862,622 B2 | 1/2011 | Dunlap et al. | |
| 7,942,935 B2 | 5/2011 | Iversen et al. | |
| 8,007,544 B2 | 8/2011 | Jonsson et al. | |
| 8,025,699 B2 | 9/2011 | Lecomte et al. | |
| 8,128,709 B2 | 3/2012 | Thorhallsdottir et al. | |
| 8,246,695 B2 | 8/2012 | Mosler | |
| 8,317,876 B2 | 11/2012 | Mosler | |
| 8,377,144 B2 | 2/2013 | Jonsson et al. | |
| 8,574,313 B2 | 11/2013 | Clausen et al. | |
| 8,764,850 B2 | 7/2014 | Hanset et al. | |
| 8,814,949 B2 | 8/2014 | Gramnaes | |
| 8,888,864 B2 | 11/2014 | Iversen et al. | |
| 8,915,969 B2 | 12/2014 | Boender | |
| 9,366,306 B2 | 6/2016 | Miyasato et al. | |
| 9,427,338 B2 | 8/2016 | Clausen et al. | |
| 9,968,467 B2 | 5/2018 | Jonsson et al. | |
| 10,821,007 B2 | 11/2020 | Albertsson et al. | |
| 10,980,648 B1 | 4/2021 | Lecomte et al. | |
| 11,446,164 B1 | 9/2022 | Lecomte et al. | |
| 11,771,572 B2 | 10/2023 | Albertsson et al. | |
| 2005/0071018 A1 | 3/2005 | Phillips et al. | |
| 2005/0137717 A1* | 6/2005 | Gramnas | A61F 2/66 623/38 |
| 2005/0203640 A1 | 9/2005 | Christensen | |
| 2005/0273179 A1 | 12/2005 | Townsend et al. | |
| 2006/0235545 A1* | 10/2006 | Habecker | A61F 2/66 623/53 |
| 2007/0250178 A1 | 10/2007 | Wilson | |
| 2008/0306612 A1 | 12/2008 | Mosler | |
| 2009/0204229 A1 | 8/2009 | Mosley et al. | |
| 2009/0222105 A1 | 9/2009 | Clausen | |
| 2011/0264230 A1 | 10/2011 | Herr et al. | |
| 2012/0179274 A1 | 7/2012 | Christensen | |
| 2012/0271434 A1 | 10/2012 | Friesen et al. | |
| 2012/0303135 A1 | 11/2012 | Vo | |
| 2013/0218297 A1 | 8/2013 | Nordman, Jr. et al. | |
| 2014/0249652 A1 | 9/2014 | Taszreak | |
| 2015/0257902 A1 | 9/2015 | Martin | |
| 2015/0328020 A1 | 11/2015 | Clausen et al. | |
| 2015/0351938 A1 | 12/2015 | Moser et al. | |
| 2016/0008147 A1 | 1/2016 | Marlin | |
| 2016/0033053 A1 | 2/2016 | Battlogg et al. | |
| 2016/0143750 A1 | 5/2016 | Kranner et al. | |
| 2016/0158030 A1 | 6/2016 | Doddroe et al. | |
| 2016/0310298 A1* | 10/2016 | Jonsson | A61F 2/66 |
| 2017/0049584 A1 | 2/2017 | Pusch et al. | |
| 2017/0051808 A1 | 2/2017 | Bogrash et al. | |
| 2017/0128236 A1 | 5/2017 | Meyer et al. | |
| 2018/0092761 A1* | 4/2018 | Rouse | A61F 2/6607 |
| 2019/0125552 A1 | 5/2019 | Day et al. | |
| 2021/0077281 A1 | 3/2021 | Albertsson et al. | |
| 2022/0273466 A1 | 9/2022 | Nijman et al. | |
| 2023/0285168 A1 | 9/2023 | Albertsson et al. | |
| 2024/0041621 A1 | 2/2024 | Albertsson et al. | |

FOREIGN PATENT DOCUMENTS

| | | |
|---|---|---|
| DE | 22 41 971 | 3/1974 |
| DE | 200 15 175 | 12/2000 |
| DE | 299 12 832 | 12/2000 |
| DE | 200 19 178 | 2/2002 |
| EP | 0 648 479 | 4/1995 |
| EP | 2 944 290 | 11/2015 |
| FR | 1 169 280 | 9/1958 |
| FR | 2 658 717 | 8/1991 |
| KR | 2000-0000930 | 1/2000 |
| KR | 2000-0047310 | 7/2000 |
| KR | 2002-0041137 | 6/2002 |
| SE | 9400380-3 | 8/1995 |
| WO | WO 94/010942 | 5/1994 |
| WO | WO 01/006965 | 2/2001 |
| WO | WO 02/064067 | 8/2002 |
| WO | WO 2016/044801 | 3/2016 |
| WO | WO 2017/077541 | 5/2017 |
| WO | WO 2022/180516 | 9/2022 |
| WO | WO 2023/170590 | 9/2023 |

OTHER PUBLICATIONS

Invitation to Pay Additional Fees in PCT Application No. PCT/US2017/064066, dated Mar. 21, 2018.

International Search Report and Written Opinion in PCT Application No. PCT/US2017/064066, dated May 24, 2018.

International Preliminary Report on Patentability and Written Opinion in PCT Application No. PCT/US2017/064066, dated Jun. 13, 2019.

Merlette et al., "The Springlite Foot, The Design Process for a Novel Advanced Composite Prosthesis", Composites in Manufacturing: Case Studies, Society of Manufacturing Engineers, 1991, pp. 269-288.

* cited by examiner

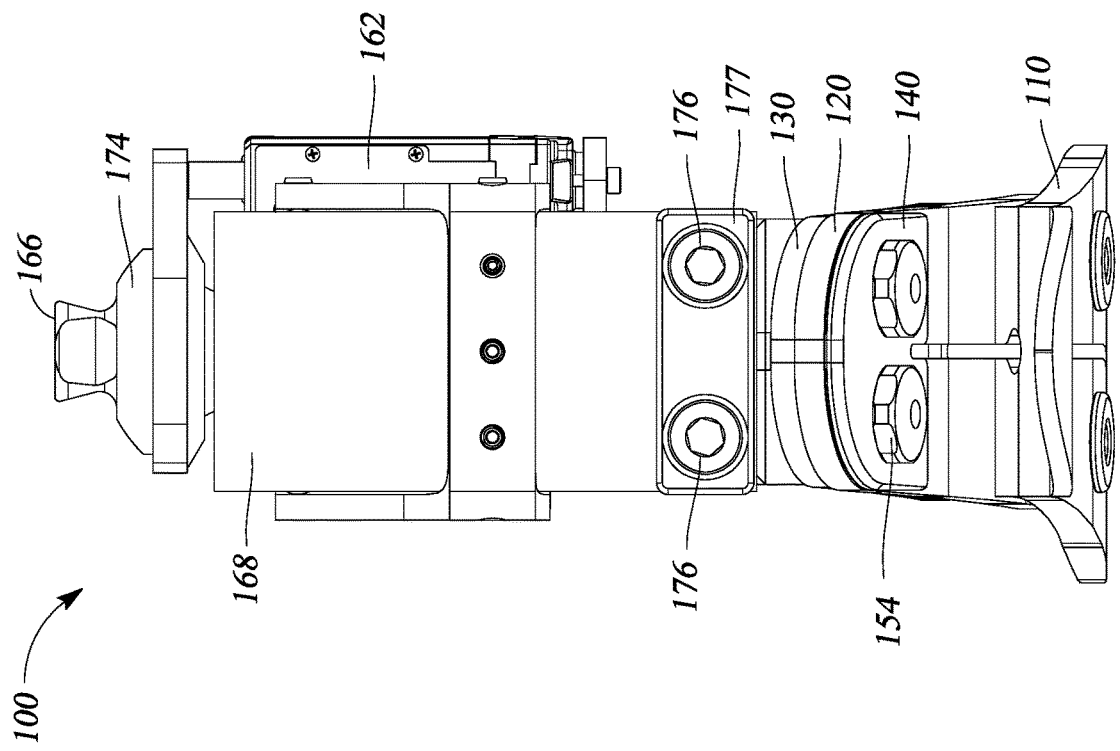
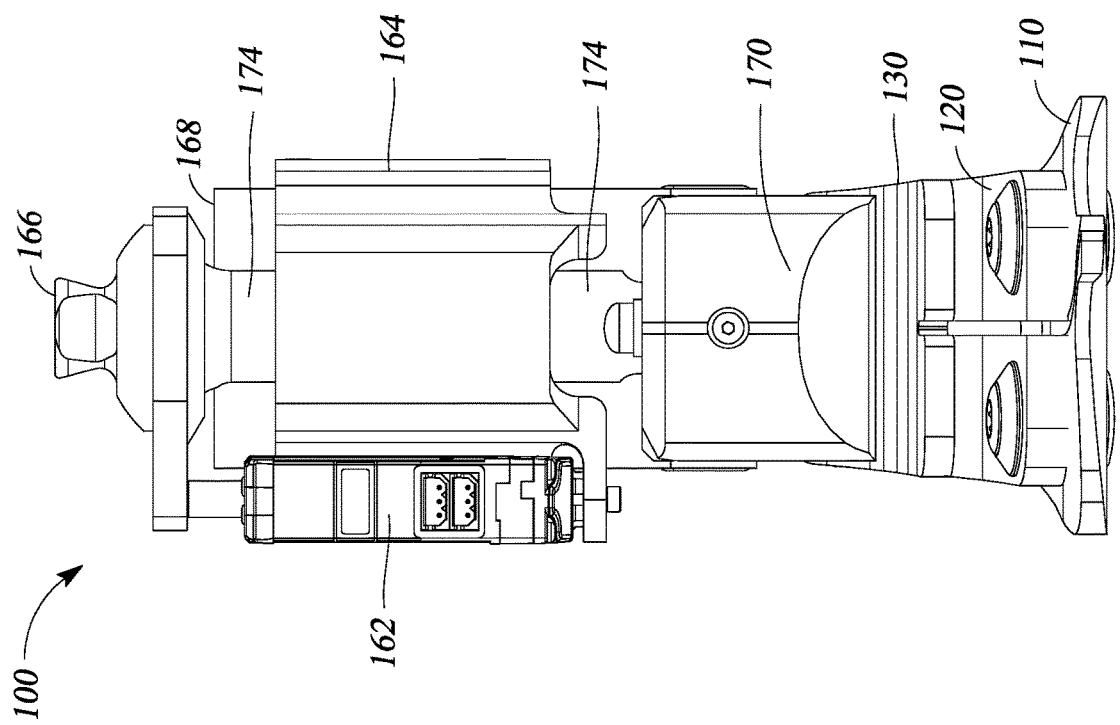

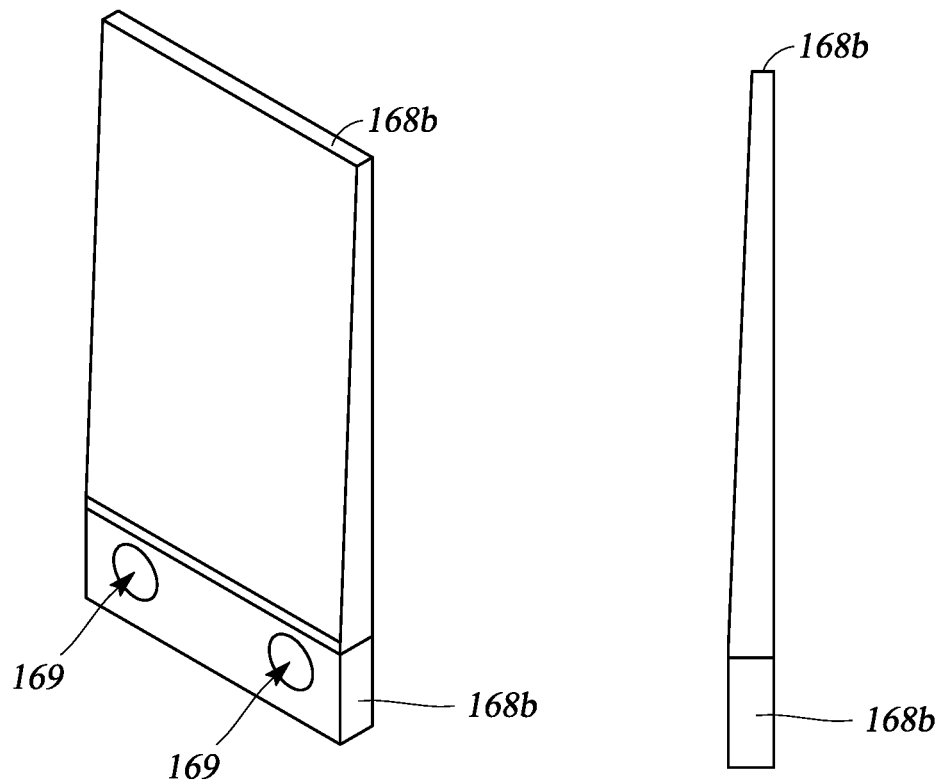
*FIG. 4A*  *FIG. 4B*

| | | |
|---|---|---|
| E | Flexural Modulus | 50 GPa |
| I | Second Movement of Area of leaf spring | 50 GPa |
| LB | Length of Heel | From 54 to 74 mm |
| | Length of Heel | From 20 to 40 mm |
| LG | Length of heel support to pivot | From 67 to 87 mm |
| | Length of heel support to pivot | From 33 to 53 mm |

FIG. 7B

| Samples - Heel and Toe (Keel) Tests | |
|---|---|
| 1 | ESAR Foot |
| 2 | Ankle Unit - softest setting |
| 3 | Ankle Unit - mid setting |
| 4 | Ankle Unit - stiffest setting |
| 5 | ESAR Foot Elements + Ankle Unit - softest setting |
| 6 | ESAR Foot Elements + Ankle Unit - mid setting |
| 7 | ESAR Foot Elements + Ankle Unit - stiffest setting |
| | Pro-Flex LP category 5 size 27 |
| | Variable stiffness unit only |
| | Variable Stiffness unit mounted on an ESAR foot |

FIG. 8A

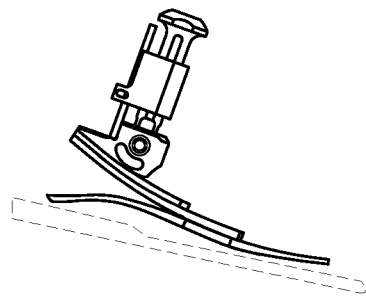 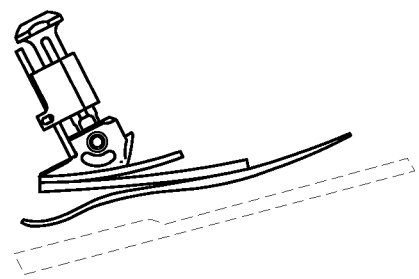
*FIG. 10A*  *FIG. 10B*
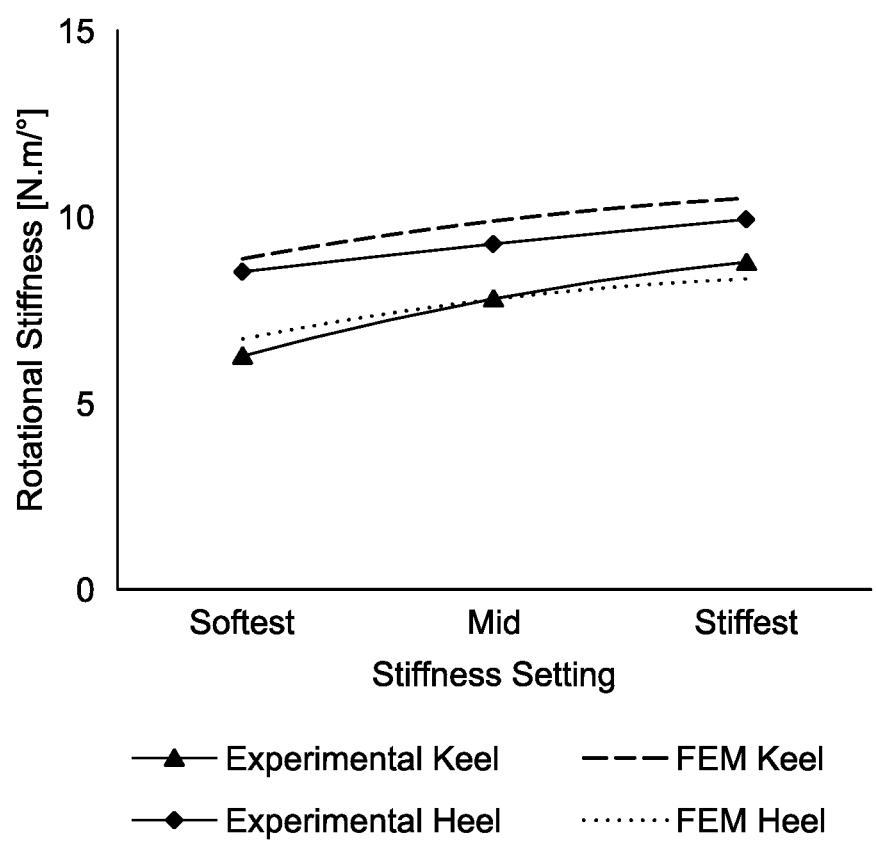
*FIG. 10C*

| | Plantarflexion [N.m/°] | | | | | | Dorsiflexion [N.m/°] | | | | | |
|---|---|---|---|---|---|---|---|---|---|---|---|---|
| | FEM | | Machine-based | | Biomechanical | | FEM | | Machine-based | | Biomechanical | |
| Variable Stiffness Prosthetic foot - softest | 6,7 | 100% | 6,3 | 100% | 3,6 | 100% | 8,9 | 100% | 8,5 | 100% | 6,2 | 100% |
| Variable Stiffness Prosthetic foot - mild | 7,8 | 116% | 7,8 | 124% | 3,7 | 103% | 9,9 | 112% | 9,3 | 109% | 6,6 | 106% |
| Variable Stiffness Prosthetic foot - siffest | 8,3 | 124% | 8,8 | 139% | 3,9 | 108% | 10,5 | 118% | 9,9 | 116% | 6,9 | 112% |

*FIG. 11*

PROSTHETIC FOOT WITH VARIABLE STIFFNESS ANKLE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit of U.S. Provisional Application No. 63/071,604, filed Aug. 28, 2020, the entirety of which is hereby incorporated by reference herein.

BACKGROUND

Field

The present application relates to foot prostheses in general, and more particularly, to prosthetic feet configured to allow for semi-active adjustments of the ankle stiffness.

Description of the Related Art

Amputation is a life transforming experience. Because the selection of an appropriate prosthetic device may have a critical impact on the rehabilitation outcomes for amputees, it would be more beneficial to make the selection thoughtfully. For lower limb amputees, the ankle functions of certain current prosthetic feet can lead to altered movement patterns, with undesirable compensation in proximal joints and the contralateral limb.

SUMMARY

If a prosthetic foot has fixed stiffness, the prosthetic foot may not allow a certified prosthetist and orthotist (CPO) to fine-tune or adjust the foot's response to the amputee assessment during first fitting or follow-up visits. The prosthetic foot with fixed stiffness cannot adapt to different terrains, walking speed, and/or the amputee's preferences. As a result, satisfaction of the amputee can be affected by the lack of ability to make such fine-tuning or adjustments.

To address the limitation of fixed stiffness of a prosthetic foot, hydraulic prosthetic feet have been developed with adjustable dorsi- and plantarflexion by varying the system's damping. Other active-control feet have also been designed, which can provide, for example, active stiffness adaptation. However, feet with active design can have additional complexity and weight.

Adaptive stiffness in a prosthetic foot can better aid an amputee in performing daily activities, including tasks such as carrying a load. In addition, amputees typically prefer lightweight prosthetic designs and/or prosthetic feet with a volume and/or dimensions closer to their missing limb. Prosthetic feet with quasi-passive or semi-active design to control stiffness can provide variable stiffness of the feet while reducing the amount of weight and complexity compared to prosthetic fee with active design. The present disclosure provides a prosthetic foot including a user-controlled variable stiffness ankle. In some embodiments, the prosthetic foot disclosed herein can modulate stiffness of the foot in response to user inputs. The ability of a user (for example, the amputee him-/herself, the medical professional such as the CPO, the amputee's caretaker or family, or anyone else) to fine-tune the stiffness according to the amputee's walking speed, terrain, and/or preferences can improve the dynamic functional properties of a prosthetic foot and satisfaction of the amputee.

In some embodiments, the variable stiffness ankle of the prosthetic foot disclosed herein can allow a range of about 20% to about 50% stiffness change in the sagittal plane from the softest to the stiffest setting. The adjustment can be done by the user, for example wirelessly via a remote user control device (e.g., smartphone, tablet computer) and/or directly on the ankle. The adjustment of stiffness can be in the sagittal plane (that is, in the anterior-posterior direction) of the prosthetic foot. Stiffness in the sagittal plane plays a significant role in the ankle stiffness and the power term at the ankle.

In some embodiments, a prosthetic ankle with variable stiffness and configured to couple a plurality of foot elements can comprise an adapter configured to operably couple to a user's limb; a base configured to couple to one or more of the plurality of foot elements; a pylon extending between the adapter and the base, the pylon comprising a longitudinal axis and first and second ends along the longitudinal axis, the first end fixedly coupled to the adapter and the second end rotatably coupled to the base; at least one cantilever spring having a first end fixedly coupled to the base and a free second end extending toward the first end of the pylon; and a slider configurable to be movable relative to the longitudinal axis of the pylon in response to a user input, the slider including a first contact location and a second contact location for the at least one cantilever spring, the first and second contact locations spaced apart from each other and positioned between the first end and the free second end of the at least one cantilever spring, wherein movements of the slider relative to the longitudinal axis of the pylon can be configured to vary positions of the first and second contact locations so as to vary a stiffness of the prosthetic ankle.

In some embodiments, the ankle can further comprise a motor configured to move the slider relative to the longitudinal axis of the pylon.

In some embodiments, the motor can comprise a linear servo motor.

In some embodiments, the ankle can further comprise a processor configured to monitor a position of the slider relative to the longitudinal axis of the pylon.

In some embodiments, the ankle can further comprise a wireless transmitter and/or receiver configured to transmit the monitored position to a remote user control device.

In some embodiments, the processor can be configured to receive user instructions input by a user on the remote user control device via the wireless transmitter and/or receiver, the user input comprising the received user instructions.

In some embodiments, the processor can be configured to adjust the position of the slider based on the received user instructions.

In some embodiments, the ankle can further comprise a knob, the user input comprising a user manually manipulating the knob to manually move the slider relative to the longitudinal axis of the pylon.

In some embodiments, the second contact location can be closer to the base than the first contact location.

In some embodiments, the first and second contact locations can be on opposite sides of the at least one cantilever spring, the at least one cantilever spring supported by the second contact location when the adapter is rotated about the second end of the pylon away from the at least one cantilever spring, and the at least one cantilever spring supported by the first contact location when the adapter is rotated about the second end of the pylon toward the at least one cantilever spring.

In some embodiments, the at least one cantilever spring can comprise a taper from the second free end toward the first end of the spring.

In some embodiments, the at least one cantilever spring can comprise a first cantilever spring and a second cantilever spring on opposite sides of the pylon, the first contact location configured to support the first cantilever spring and the second contact location configured to support the second cantilever spring.

In some embodiments, the first and second cantilever springs can be supported by the first and second contact locations relatively when the pylon rotates about the second end of the pylon in a first direction, and only the first cantilever spring is supported by the first contact location when the pylon rotates about the second end of the pylon in a second direction opposite the first direction.

In some embodiments, a prosthetic foot can comprise any of the prosthetic ankle embodiments described above, a lower foot member, the lower foot member comprising a toe end and a heel end; and an intermediate foot member located between the lower foot member and the prosthetic ankle, the intermediate foot member having a proximal end and a distal end, the base of the prosthetic ankle fixed coupled to the intermediate foot member at or near the proximal end, the lower foot member coupled to the intermediate foot member at or near the distal end.

In some embodiments, the distal end of the intermediate foot member can terminate proximal to the toe end of the lower foot member.

In some embodiments, the intermediate foot member can comprise a taper so that a thickness of the intermediate foot member increases from the proximal end to the distal end.

In some embodiments, further comprising an upper foot member located between the intermediate foot member and the prosthetic ankle, the upper foot member having a proximal end and a distal end, the base of the prosthetic ankle fixed coupled to the upper foot member at or near the proximal end of the upper foot member.

In some embodiments, the distal end of the upper foot member can be separated from the distal end of the intermediate foot member by a gap when the prosthetic foot is resting on a level surface.

In some embodiments, the at least one cantilever spring can be supported by the second contact location when the prosthetic foot is in dorsiflexion.

In some embodiments, the at least one cantilever spring can be supported by the first contact location when the prosthetic foot is in plantarflexion.

In some embodiments, for a given location of the slider relative to the longitudinal axis of the pylon, the stiffness of the prosthetic ankle can be lower when the prosthetic foot is in plantarflexion than when the prosthetic foot is in dorsiflexion.

In some embodiments, a prosthetic ankle with variable stiffness and configured to couple a prosthetic foot can comprise an adapter configured to operably couple to a user's limb; a base configured to couple to one or more of the plurality of foot elements; a pylon extending between the adapter and the base, the pylon comprising a longitudinal axis and first and second ends along the longitudinal axis, the first end coupled to the adapter and the second end coupled to the base; at least one cantilever spring having a first end fixedly coupled to the base and a free second end extending toward the first end of the pylon, the at least one cantilever spring comprising a taper from the second free end toward the first end of the spring; and a slider configurable to be movable relative to the longitudinal axis of the pylon in response to a user input, the slider including at least one contact location for the at least one cantilever spring, the at least one contact location positioned between the first end and the free second end of the at least one cantilever spring, wherein movements of the slider relative to the longitudinal axis of the pylon can be configured to vary a position of the at least one contact location so as to vary a stiffness of the prosthetic ankle.

In some embodiments, the ankle can further comprise a motor configured to move the slider relative to the longitudinal axis of the pylon.

In some embodiments, the motor can comprise a linear servo motor.

In some embodiments, the ankle can further comprise a processor configured to monitor a position of the slider relative to the longitudinal axis of the pylon.

In some embodiments, the ankle can further comprise a wireless transmitter and/or receiver configured to transmit the monitored position to a remote user control device.

In some embodiments, the processor can be configured to receive user instructions input by a user on the remote user control device via the wireless transmitter and/or receiver, the user input comprising the received user instructions.

In some embodiments, the processor can be configured to adjust the position of the slider based on the received user instructions.

In some embodiments, the ankle can further comprise a knob, the user input comprising a user manually manipulating the knob to manually move the slider relative to the longitudinal axis of the pylon.

In some embodiments, the at least one contact location can comprise a first contact location and a second contact location for the at least one cantilever spring, the first and second contact locations spaced apart from each other and positioned between the first end and the free second end of the at least one cantilever spring.

In some embodiments, the second contact location can be closer to the base than the first contact location.

In some embodiments, the first and second contact locations can be on opposite sides of the at least one cantilever spring, the at least one cantilever spring supported by the second contact location when the adapter is rotated about the second end of the pylon away from the at least one cantilever spring, and the at least one cantilever spring supported by the first contact location when the adapter is rotated about the second end of the pylon toward the at least one cantilever spring.

In some embodiments, the at least one cantilever spring can comprise a first cantilever spring and a second cantilever spring.

In some embodiments, the first and second cantilever springs can be located on opposite sides of the pylon, the slider including a first contact location for the first cantilever spring and a second contact location for the second cantilever spring.

In some embodiments, the first and second cantilever can be supported by the first and second contact locations relatively when the pylon rotates about the second end of the pylon in a first direction, and only the first cantilever is supported by the first contact location when the pylon rotates about the second end of the pylon in a second direction opposite the first direction.

In some embodiments, a prosthetic foot can comprise any of the prosthetic ankle embodiments described above, a lower foot member, the lower foot member comprising a toe end and a heel end; and an intermediate foot member located between the lower foot member and the prosthetic ankle, the intermediate foot member having a proximal end and a distal end, the base of the prosthetic ankle fixed coupled to the intermediate foot member at or near the proximal end, the lower foot member coupled to the intermediate foot member at or near the distal end.

In some embodiments, the distal end of the intermediate foot member can terminate proximal to the toe end of the lower foot member.

In some embodiments, the intermediate foot member can comprise a taper so that a thickness of the intermediate foot member increases from the proximal end to the distal end.

In some embodiments, further comprising an upper foot member located between the intermediate foot member and the prosthetic ankle, the upper foot member having a proximal end and a distal end, the base of the prosthetic ankle fixed coupled to the upper foot member at or near the proximal end of the upper foot member.

In some embodiments, the distal end of the upper foot member can be separated from the distal end of the intermediate foot member by a gap when the prosthetic foot is resting on a level surface.

In some embodiments, for a given location of the slider relative to the longitudinal axis of the pylon, the stiffness of the prosthetic ankle can be lower when the prosthetic foot is in plantarflexion than when the prosthetic foot is in dorsiflexion.

In some embodiments, a prosthetic foot with variable ankle stiffness can comprise at least one foot element, the at least one foot element defining a toe end of the prosthetic foot and a heel end of the prosthetic foot, a sagittal plane extending from the toe end and the heel end; a variable stiffness ankle unit comprising: an adapter configured to operably couple to a user's limb; a base configured to couple to one or more of the plurality of foot elements; a pylon extending between the adapter and the base, the pylon comprising a longitudinal axis and first and second ends along the longitudinal axis, the first end fixedly coupled to the adapter and the second end rotatably coupled to the base so that the pylon is configured to rotate about the second end in the sagittal plane of the prosthetic foot; at least one cantilever spring having a first end fixedly coupled to the base and a free second end extending toward the first end of the pylon, the at least one cantilever spring having a width generally perpendicular to a length extending from the first end to the free second end of the spring, wherein the width of the at least one cantilever spring can be generally perpendicular to the sagittal plane of the prosthetic foot; and a slider configurable to be movable relative to the longitudinal axis of the pylon in response to a user input, the slider including at least one contact location for the at least one cantilever spring, the at least one contact location positioned between the first end and the free second end of the at least one cantilever spring, wherein movements of the slider relative to the longitudinal axis of the pylon can be configured to vary a position of the at least one contact location so as to vary a stiffness of the prosthetic ankle in the sagittal plane.

In some embodiments, the at least one foot element can comprise a lower foot member, the lower foot member comprising a toe end defining the toe end of the prosthetic foot and a heel end defining the heel end of the prosthetic foot; and an intermediate foot member located between the lower foot member and the ankle unit, the intermediate foot member having a proximal end and a distal end, the base of the prosthetic ankle fixed coupled to the intermediate foot member at or near the proximal end, the lower foot member coupled to the intermediate foot member at or near the distal end.

In some embodiments, the distal end of the intermediate foot member can terminate proximal to the toe end of the lower foot member.

In some embodiments, the intermediate foot member can comprise a taper so that a thickness of the intermediate foot member increases from the proximal end to the distal end.

In some embodiments, further comprising an upper foot member located between the intermediate foot member and the prosthetic ankle, the upper foot member having a proximal end and a distal end, the base of the prosthetic ankle fixed coupled to the upper foot member at or near the proximal end of the upper foot member.

In some embodiments, the distal end of the upper foot member can be separated from the distal end of the intermediate foot member by a gap when the prosthetic foot is resting on a level surface.

In some embodiments, the at least one cantilever spring comprising a taper from the second free end toward the first end of the spring.

In some embodiments, the foot can further comprise a motor configured to move the slider relative to the longitudinal axis of the pylon.

In some embodiments, the motor can comprise a linear servo motor.

In some embodiments, the foot can further comprise a processor configured to monitor a position of the slider relative to the longitudinal axis of the pylon.

In some embodiments, the foot can further comprise a wireless transmitter and/or receiver configured to transmit the monitored position to a remote user control device.

In some embodiments, the processor can be configured to receive user instructions input by a user on the remote user control device via the wireless transmitter and/or receiver, the user input comprising the received user instructions.

In some embodiments, the processor can be configured to adjust the position of the slider based on the received user instructions.

In some embodiments, the foot can further comprise a knob, the user input comprising a user manually manipulating the knob to manually move the slider relative to the longitudinal axis of the pylon.

In some embodiments, the at least one contact location can comprise a first contact location and a second contact location for the at least one cantilever spring, the first and second contact locations spaced apart from each other and positioned between the first end and the free second end of the at least one cantilever spring.

In some embodiments, the second contact location can be closer to the base than the first contact location.

In some embodiments, the first and second contact locations can be on opposite sides of the at least one cantilever spring, the at least one cantilever spring supported by the second contact location when the adapter is rotated about the second end of the pylon away from the at least one cantilever spring, and the at least one cantilever spring supported by the first contact location when the adapter is rotated about the second end of the pylon toward the at least one cantilever spring.

In some embodiments, the at least one cantilever spring can comprise a first cantilever spring and a second cantilever spring.

In some embodiments, the first and second cantilever springs can be located on opposite sides of the pylon, the slider including a first contact location for the first cantilever spring and a second contact location for the second cantilever spring.

In some embodiments, the first and second cantilever can be supported by the first and second contact locations relatively when the pylon rotates about the second end of the pylon in a first direction, and only the first cantilever is supported by the first contact location when the pylon rotates about the second end of the pylon in a second direction opposite the first direction.

In some embodiments, for a given location of the slider relative to the longitudinal axis of the pylon, the stiffness of the prosthetic ankle can be lower when the prosthetic foot is in plantarflexion than when the prosthetic foot is in dorsiflexion.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 2E illustrates a front view of the prosthetic foot of FIG. 1A.

FIG. 2F illustrates a rear view of the prosthetic foot of FIG. 1A.

FIG. 4A illustrates a perspective view of an example cantilever spring.

FIG. 4B illustrates a side view of the cantilever spring of FIG. 4A.

FIG. 7B is a table listing the mechanical parameters of the prosthetic foot of FIG. 7A.

FIG. 8A is a table listing samples tested during machine-based testing.

FIGS. 10A-10C illustrate a finite element model (FEM) of a variable stiffness prosthetic foot of the present disclosure and simulation results.

FIG. 11 is a table summarizing test results of the machine-based tests illustrated in FIGS. 8A-8C, the biomechanical study, and the FEM simulation using example prosthetic feet with a one-spring design.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Overview of Example Prosthetic Feet

The present disclosure provides examples of a prosthetic foot with quasi-passive or semi-active design, allowing a user to adjust a stiffness of the foot with less complex and/or less bulky design than a prosthetic foot with active design. Throughout the disclosure, a prosthetic foot with a passive design does not include any powered components so that any movement of foot is actuated manually by the amputee or any user (such as the CPO). Throughout the disclosure, a prosthetic foot with an active design is a fully automated prosthesis. Throughout the disclosure, a prosthetic foot with a quasi-passive or semi-active design is capable of altering behavior using sensor(s) and microprocessor technology but is simpler and lighter than an active prosthetic foot.

In some examples, the overall height of the prosthetic foot of the present disclosure does not exceed about 200 mm, or about 190 mm, or about 180 mm, or about 170 mm, or about 160 mm. In some examples, the weight of the prosthetic foot of the present disclosure (including a battery and a control system as described below) does not exceed about 1.8 kg, or about 1.7 kg, or about 1.6 kg, or about 1.5 kg, or about 1.4 kg, or about 1.3 kg, or about 1.2 kg. In some examples, the volume of the prosthetic foot of the present disclosure is configured to be comparable with (e.g., equal to or less) that of the amputee's calf.

Figure 1A:
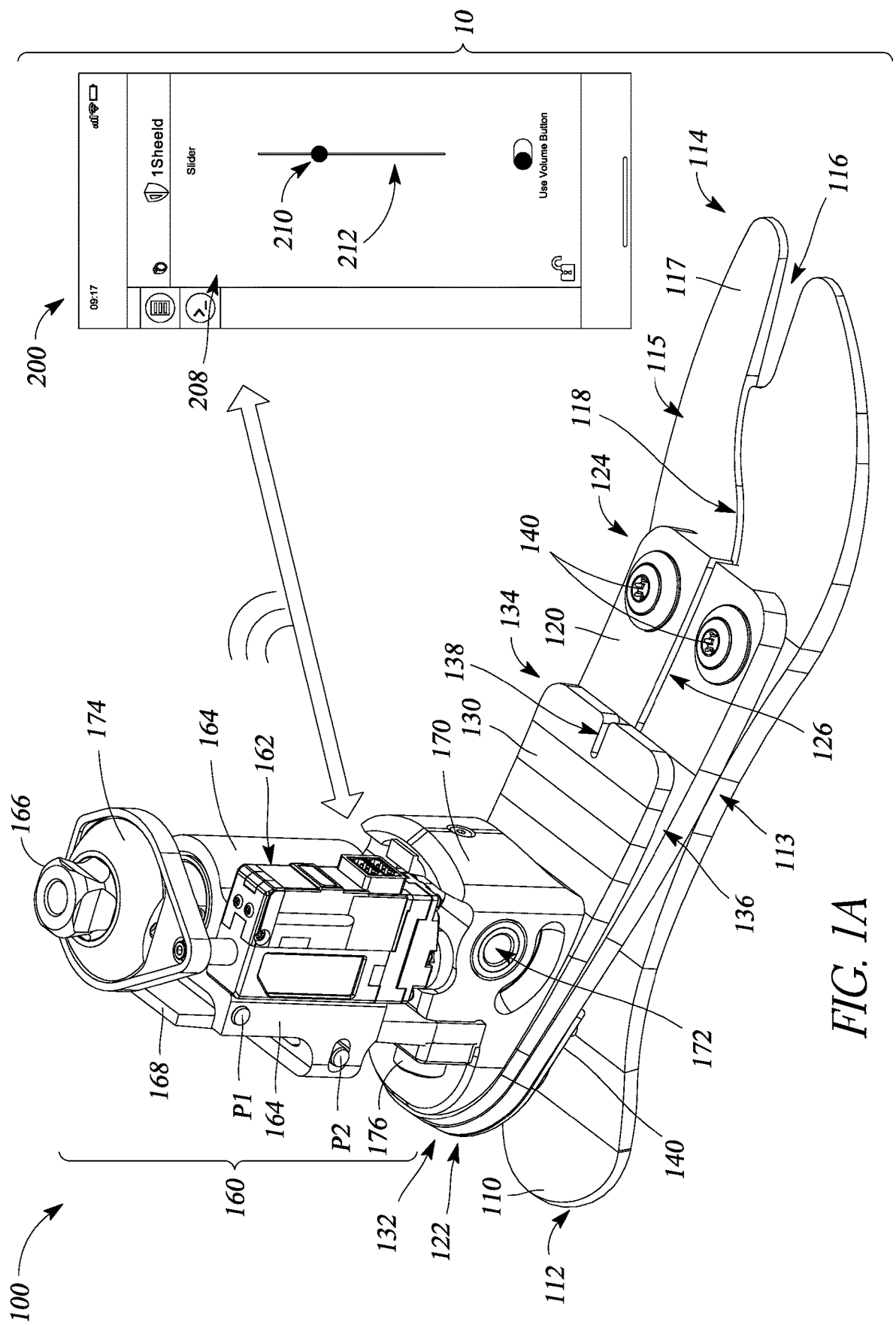
FIG. 1A illustrates a prosthetic system including an example variable stiffness prosthetic foot in wireless communication with an electronic user control device.

In some embodiments, the prosthetic foot disclosed herein allows remote control by the user to adjust the stiffness. As shown in FIG. 1A, an example prosthetic system 10 can include a variable stiffness prosthetic foot 100 and a user control device 200. In some embodiments, the user control device 200 can include a smartphone, a smartwatch, a tablet, a laptop, or any other computing device that includes a display device (e.g., electronic display screen) and is configured to receive user inputs.

The prosthetic foot 100 can include a plurality of foot members 110, 120, 130 and a variable stiffness ankle unit 160. The variable stiffness ankle unit 160 can include an adapter 166 configured to couple the foot 100 to a user's residual limb (for example, via a socket, pylon, etc.). The variable stiffness ankle unit 160 can be controlled based on user inputs. The user can input user instructions via a user control device 200, which can be in electrical communication with the prosthetic foot 100. The electrical communication can be preferably wireless, and more preferably via BLUETOOTH® technology, although any other suitable wireless communication protocols can be implemented. In some embodiments, the electrical communication can be via a wired connection, such as shown in FIG. 1D. For example, a medical profession (such as a CPO) can attach one end of a cable 300 to a connector in the electronics of the ankle unit 160, such as directly to the electronics of the motor 162 or optionally to a processor 192. An opposite end of the cable 300 can be connected electrically to a user control device or user interface 200. In some implementations, the user interface can include a digital and/or manual user input (such as a dial, a button, or otherwise) to receive a user input from the medical professional. The user input can be transmitted via the cable to the ankle unit 160 to adjust the stiffness of the ankle unit 160.

As shown in FIG. 1A, the user control device 200 can run an application or software to display a slider function. A location of a slider button 210 relative to a sliding bar 212 can indicate the stiffness of the ankle unit. In some embodiments, a higher location of the slider button 210 can indicate a higher stiffness and a lower location of the slider button 210 can indicate a lower stiffness. In one example, the slider bar 212 can indicate a continuous range of 0% stiffness to 100% stiffness. In some embodiments, the slider bar 212 may include discrete stiffness levels, such as softest, mid stiffness, and stiffest, or otherwise. In some embodiments, the softest level can correspond to 0%-10%, or 0% stiffness. In some embodiments, the mid-stiffness level can correspond to about 43%-53%, or about 50% stiffness. In some embodiments, the stiffest level can correspond to 90%-100%, or 100% stiffness. Other visual, audio, and/or haptic indicators of the ankle stiffness can optionally be included on the user control device 200.

The user can moving the slider button 210 by a finger gesture made on the display screen 208, which can be a touchscreen, of the user control device 200. For example, the finger gesture can include a touch of a desired location of the slider button 210 on the sliding bar 212, a drag of the slider button 210 along the sliding bar 212 until the desired location of the slider button 210 is reached, or otherwise. Additionally or alternatively, the user can use any control buttons on the user control device 200, for example, the volume-up and/or volume-down buttons or otherwise, to move the slider button 210 upward or downward along the sliding bar 212. In some embodiments, the display screen 208 of the user control device 200 include an option to display a log of a history of the user adjusting the ankle stiffness of the prosthetic foot 200 using the user control device 200. FIG. 1A shows the sliding bar 212 as a vertical bar. In another implementation, the sliding bar can be oriented horizontally on the display screen 208. In another implementation, the slider bar 212 can be curved or circular (for example, in a speedometer or fuel gauge type of visualization). Other suitable user interfaces can be used instead of the bar 212 to adjust the stiffness level.

Figure 1B:
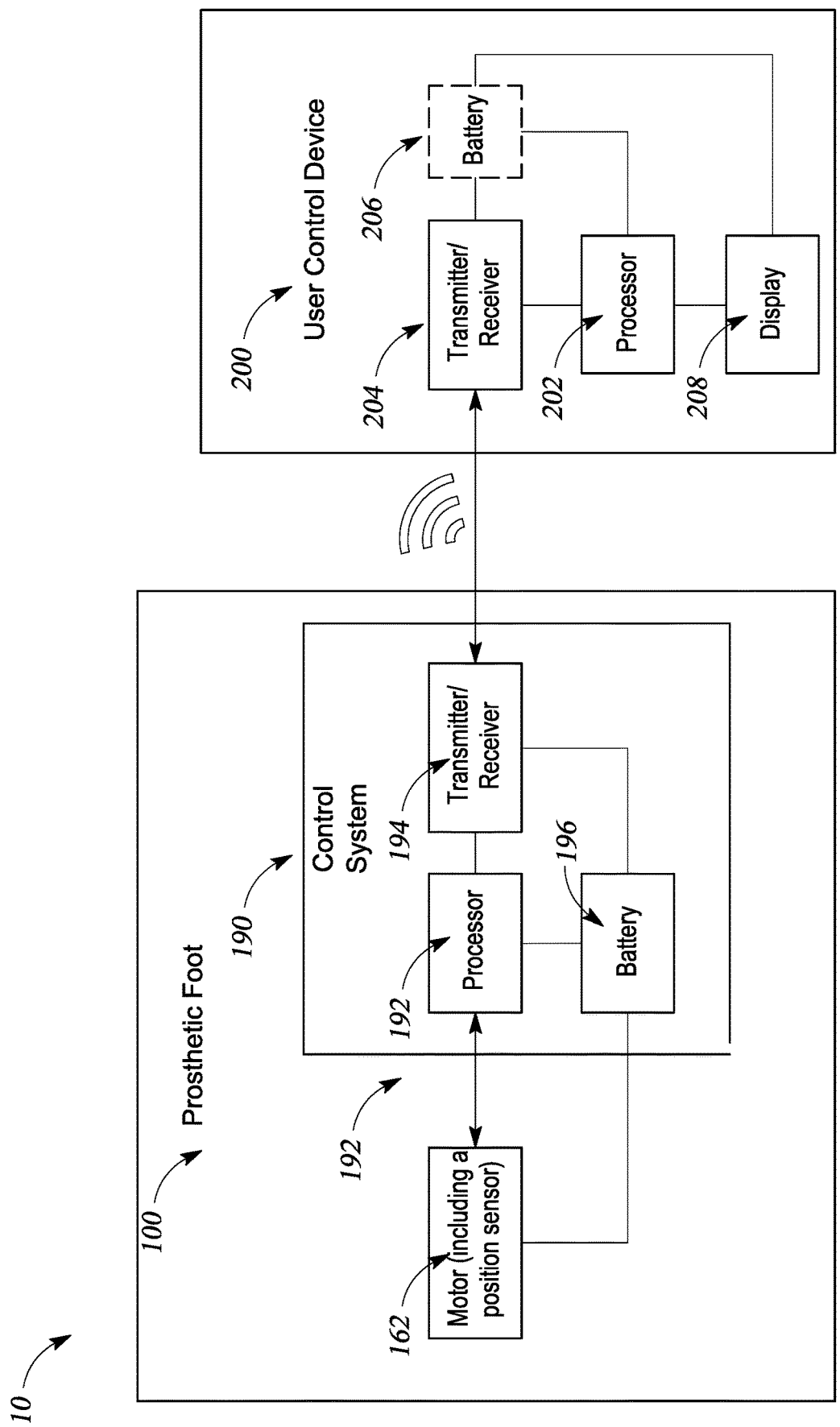
FIG. 1B illustrates schematically example electronic components of the prosthetic system of FIG. 1A.

In some embodiments such as shown in FIG. 1B, the prosthetic foot 100 can include a wireless transmitter and/or receiver 194 (including a transceiver) that can wirelessly communicate with a wireless transmitter and/or receiver 204 of the user control device 200. In some embodiments, the wireless transmitter and/or receiver 194 can include a BLUETOOTH® module, for example, a BLUETOOTH® shield (1Shield, USA). The wireless transmitter and/or receiver 194 can be part of a control system 190 of the prosthetic foot 190. The control system 190 can include a processor 192. The processor 192 can be in or on a printed power circuit or printed circuit board (PCB). In one example, the processor 192 can include an Arduino Mega microcontroller board (Arduino, Italy). In some embodiments, the control system 190 can be located at the variable stiffness ankle unit 160. In some embodiments, the control system 190 can located at a different location of the prosthetic foot 100.

As shown in FIGS. 1A and 1B, the variable stiffness ankle unit 160 of the prosthetic foot 100 can include a motor 162 (also referred to as a motorized actuator) configured to be actuated to adjust the ankle stiffness of the ankle unit 160. In some embodiments, the motor 152 can include a linear servo motor, for example, the MightyZap micro- or mini-linear servo actuator (Irrobot, South Korea). As shown in FIG. 1B, the motor 162 can include a position sensor (for example, a rotary encoder, a linear encoder, or otherwise) configured to measure the position of a motor shaft and output an electrical signal indicative of the motor shaft position.

Figure 1C:
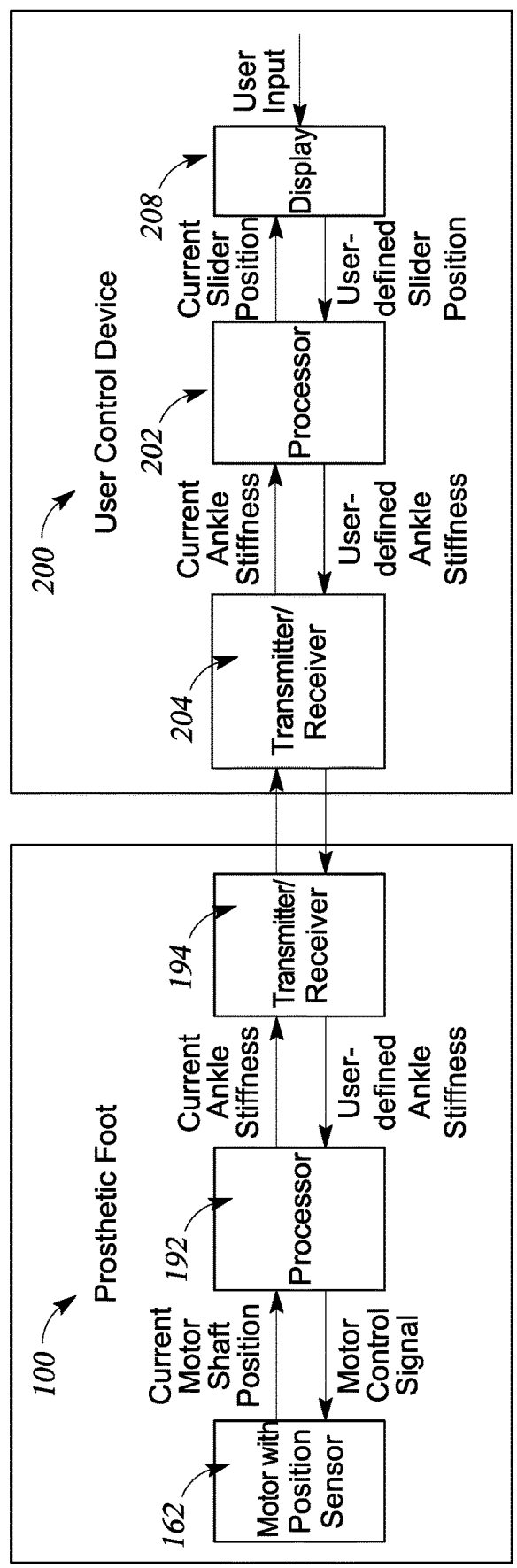
FIG. 1C illustrates schematically a block diagram of electrical communication in the prosthetic system of FIG. 1A.
Figure 1D:
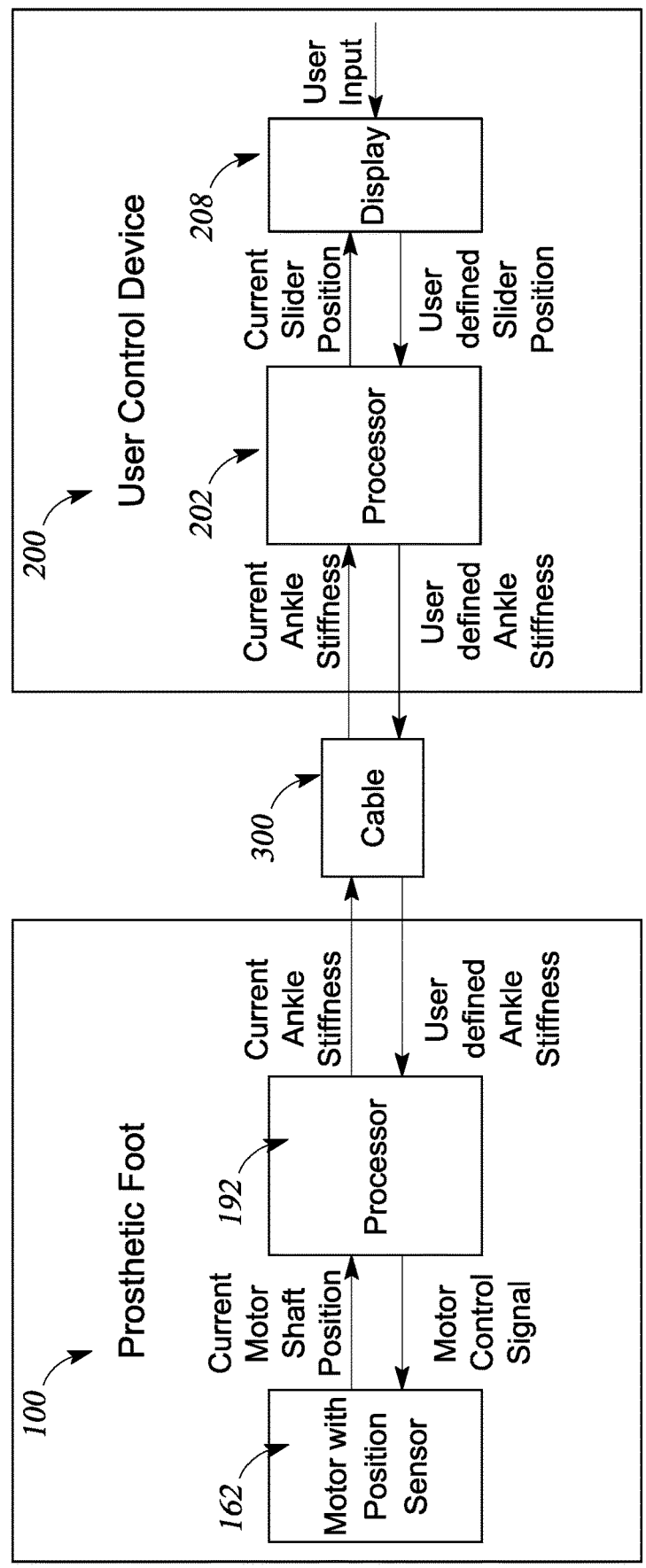
FIG. 1D illustrates schematically a block diagram of an alternative embodiment of electrical communication in the prosthetic system of FIG. 1A.

As shown in FIG. 1C, on the prosthetic foot side, the processor 192 of the control system 190 can receive an electrical signal indicative of a current motor shaft position output by the position sensor and process the signal to calculate a current ankle stiffness. In some embodiments, the current ankle stiffness value calculated by the processor 192 can include a percentage of a highest possible stiffness value of the ankle unit 160. The processor 192 can also output a motor control signal to the position sensor of the motor 162 based on a signal indicative of a user-defined ankle stiffness from the user control device 200 via the wireless transmitter/receiver 194, 204. The motor 162 can be actuated in response to the control signal to adjust the shaft position corresponding to the user-defined ankle stiffness. In some embodiments, the control signal can include a calculation of the amount of travel needed by the motor shaft to change from the current ankle stiffness to the user-defined ankle stiffness.

The control system 190 can also include a battery 196 to power the control system 190 and/or the motor 162. In some embodiments, the battery 196 can have a voltage ranging from 6V to 12V, or 9V.

On the user control device side, as shown in FIGS. 1B and 1C, the user control device 200 can include a processor 202 configured to process the signal indicative of the current ankle stiffness from the control system 190 of the prosthetic foot 100 to determine a current slider position (for example, a current ankle stiffness value ranging from 0% to 100%). The processor 202 can also receive a user input signal via the display device 208 or other user inputs (such as from buttons as described above). The user input signal can include a user-defined slider position, which the processor 202 of the user control device 200 can process so as to output a signal indicative of a user-defined ankle stiffness. As shown in FIG. 1B, the user control device 200 can optionally include a battery 206 configured to power the user control device 200.

The prosthetic foot 100 and/or the user control device 200 can include any other suitable electronic components.

Examples of Foot Members

Details of the foot members of the prosthetic foot 100 will now be described. In some embodiments, the prosthetic foot 100 can include a lower foot member 110, a tapered intermediate foot member 120, and, optionally, an upper foot member 130, which can also be tapered. In some embodiments, the lower foot member 110 is a heel-to-toe plate and extends beyond a distal end of the intermediate foot member 120. In other embodiments, the intermediate foot member can extend to a toe end, and the lower foot member can be a heel plate that extends from a heel end to a proximal end that is coupled to the intermediate foot member proximal to the toe end. The prosthetic foot can be an example of an Energy-Storing and Return (ESAR) foot. ESAR feet can improve the ankle functions. ESAR feet are often prescribed for their loading and unloading efficiency, which may be at least in part due to the compliance of different foot members in the prosthetic foot. ESAR feet may also reduce metabolic cost while increasing comfort and safety. ESAR feet can be categorized by stiffness and prescribed to the amputee in accordance with the expert advice of the healthcare provider based on the amputee's activity level and weight. One example of the foot members of the prosthetic foot of the present disclosure can include the foot members of the PRO-FLEX® LP by Össur, Iceland. Such a combination of foot members result in a low build height, which more easily accommodates an additional unit, such as the ankle unit disclosed herein, than foot members with a greater build height.

In the illustrated embodiments such as shown in FIGS. 1A and 2A-2F, the prosthetic foot 100 can include a lower foot member 110. The lower foot member 110 can be substantially plate-like and can have a generally rectangular or rectangular cross-section transverse to a longitudinal axis or the sagittal plane S (see FIG. 2A) of the foot 100 along at least a portion of its length. In some embodiments, the lower foot element 110 can be constructed of a resilient material capable of flexing in multiple directions. The lower foot element 110 can include multiple layers or laminae. Examples of possible materials for the lower foot element 110 include carbon, any polymer material, and any composite of polymer and fiber. The polymer can be thermoset or thermoplastic. In a composite, the fiber reinforcement can be any type of fiber, such as carbon, glass, or aramid, or a combination of different types of fibers. The fibers can be long and unidirectional, or they can be chopped and randomly oriented.

The lower foot member 110 can extend from a heel end 112 to a toe end 114. The heel end 112 can define a heel end of the prosthetic foot 100. The toe end 114 can define a toe end of the prosthetic foot 100. The lower foot member 110 can include an arch region 113 between the heel end 112 and the toe end 114, for example, at approximately the location of an arch of a natural human foot. The lower foot member 110 can further include a forefoot region 115 distal to the arch region 113 or between the arch region 113 and the toe end 114. In some embodiments, the forefoot region 115 is wider than the arch region 113 and/or heel end 112.

In some embodiments, a toe portion of the lower foot member 110 includes a generally U-shaped cut-out portion, slot, or gap 116 extending inwardly from the toe end 114. In some embodiments, the cut-out portion 116 can be positioned toward a medial side of the longitudinal axis of the lower foot member 110, but can be spaced from a medial edge of the lower foot member 110. The cut-out portion 116 can provide the lower foot member 110 with a "sandal toe" appearance and/or function and define a structural "big toe" in a medial portion 117.

Figure 2A:
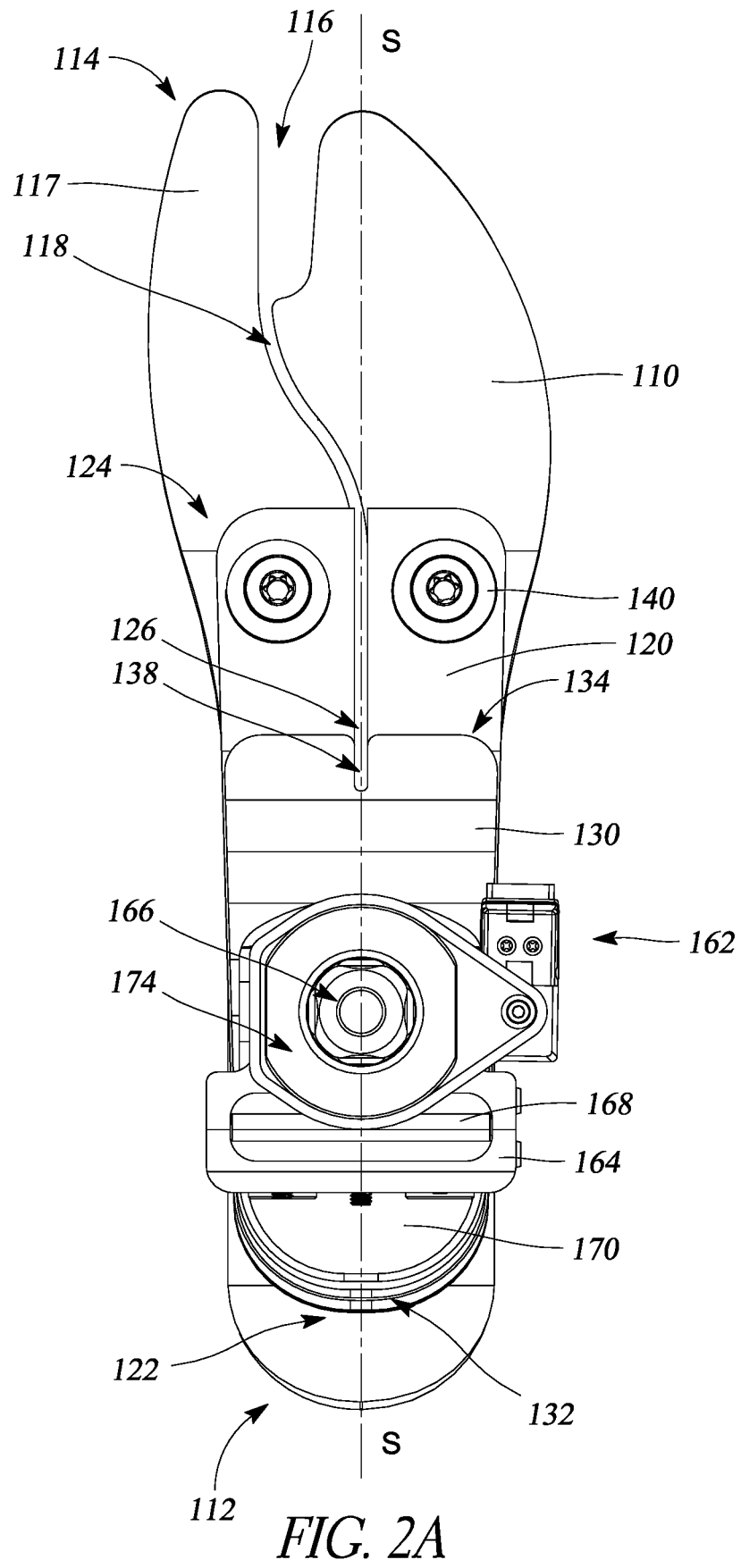
FIG. 2A illustrates a top view of the prosthetic foot of FIG. 1A.
Figure 2B:
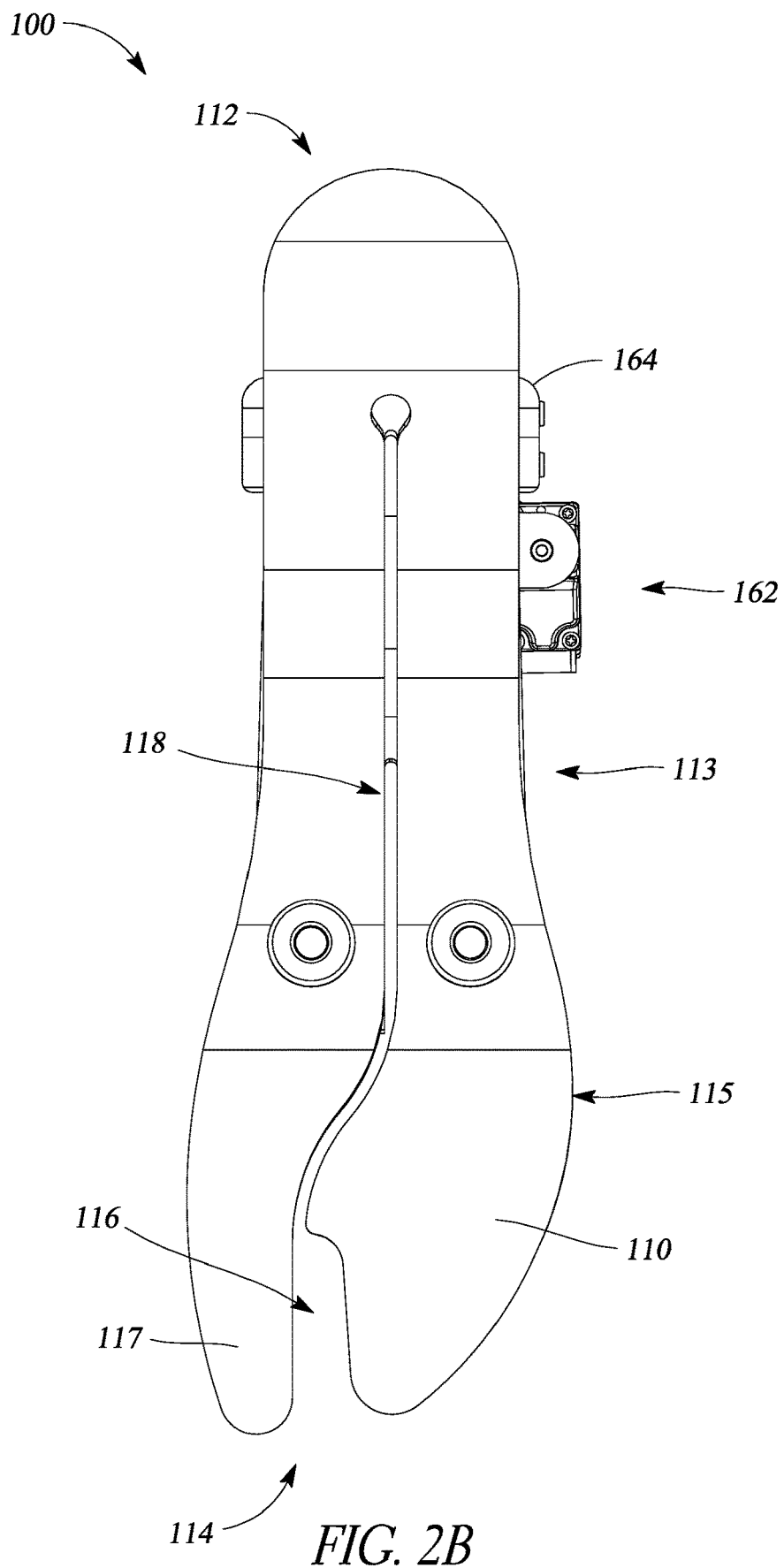
FIG. 2B illustrates a bottom view of the prosthetic foot of FIG. 1A.

In the illustrated embodiments, the lower foot member 110 can also include a split 118 that at least partially extends substantially along the longitudinal axis of the foot. The split 118 provides a narrow gap between the medial portion and a lateral portion of the lower foot member 110 and allows the medial and lateral portions to flex somewhat independently of each other. As shown in FIG. 2B, the split 118 does not extend to the heel end 112 of the lower foot member 110. In the illustrated embodiment, the split 118 extends substantially straight through the arch region 113, then curves medially in the forefoot region 115, or approximately at a border between the arch region 113 and the forefoot region 115, and extends to a base of the cut-out portion 116.

As shown in FIGS. 1A, 2A and 2C-2F, the prosthetic foot 100 can also include an intermediate foot member 120. The intermediate foot member 120 can be substantially plate-like and can have a generally rectangular or rectangular cross-section transverse to the longitudinal axis and/or the sagittal plane S along at least a portion of its length. The intermediate foot member 120 can be made of the same or similar materials as and constructed the same or similar to the lower foot member 110. The intermediate foot member 120 can extend from a proximal end 122 downward and forward to a distal end 124. In the illustrated embodiment, the intermediate foot member 120 can include a split 126 extending along at least a portion of the length of the intermediate foot member 120 to the distal end 124. The split 126 can allow medial and lateral portions of the intermediate foot member 120 to flex somewhat independently of each other. The split 126 in the intermediate foot member 120 can be aligned with the straight portion of the split 118 in the lower foot member 110. The intermediate foot member 120 is coupled to the lower member 110 with fasteners 140, e.g., bolts, positioned proximate the distal end 124 of the intermediate foot member 120. The lower foot member 110 can extend beyond or distal to the distal end 124 of the intermediate foot member 120. In the illustrated embodiment, the distal end 124 of the intermediate foot member 120 and fasteners 140 are positioned at or near a transition between the arch region 113 and forefoot region 115 of the lower foot member 110 (for example, proximate a portion of the foot 100 generally corresponding to a metatarsal region of a natural human foot).

The intermediate foot member 120 can taper (for example, gradually tape) from the distal end 124 toward the proximal end 122 such that the distal end 124 of the intermediate foot member 120 is thicker than the proximal end 122. The taper of the intermediate foot member 120 can shift the center or axis of rotation of the foot rearward and/or closer to that of a natural human ankle. This shifting can provide a smoother rollover. The prosthetic foot 100 can exhibit a greater range of ankle motion in the stance phase and flex to plantarflexion earlier in the stance phase than in a prosthetic foot where the center or axis of rotation of the foot is more forward and/or further away from that of a natural human ankle. The tapered intermediate foot member 120 can allow for quicker and smoother plantarflexion upon heel strike to foot flat in stance. The tapered intermediate foot member 120 can also allow for greater energy storage as the foot 100 dorsiflexes through stance to pre-toe-off, which allows for greater energy return during plantarflexion in toe-off and allows for a more controlled rollover.

The prosthetic foot 100 can include a shim 140 under the intermediate foot member 120. The shim can be made of a material having a greater stiffness than the material of the intermediate foot member 120. In some embodiments, the shim can include a steel plate. In some embodiments, the shim 140 can be located at or near the proximal end 122 of the intermediate foot member 120. In the illustrated embodiment, a proximal edge of the shim 540 is aligned with a proximal edge of the intermediate foot member 120. The shim 140 can be inserted between the intermediate foot member 120 and fasteners 154. As described below, the fasteners 154 can also couple the ankle unit 160 to upper and intermediate foot members 130, 120 and a base 170 of the ankle unit 170. The shim 140 can prevent flexing of the intermediate foot member 120 where flexing is undesirable. The shim 140 can also add strength and/or rigidity to the proximal end 122 of the intermediate foot member 120.

In the illustrated embodiments, the prosthetic foot 100 can also optionally include an upper foot member 130. As shown in FIGS. 1A, 2A and 2C-2F, the upper foot member 130 can extend from a proximal end 132 to a distal end 134. The upper foot element 130 can optionally be tapered (e.g., gradually tapered) from the proximal end 132 toward the distal end 134 such that the distal end 134 is thinner than the proximal end 132. In the illustrated embodiment, there can be a gap 136 between the distal end 134 of the upper foot member 130 and a top surface of the intermediate foot member 120. During the mid-stance and toe-off phases of a gait cycle, the gap 136 can close and the upper foot member 130 can engage the intermediate foot member 120, which increases the stiffness of the foot 100 and/or stores additional energy in the intermediate foot member 120 as the foot 100 moves toward toe-off. In some embodiments, the gap 136 can gradually close, providing progressive stiffening of the foot during mid-stance and toe-off. The upper foot member 130 can engage the intermediate foot member 120 when the prosthetic foot 100 is placed under load and advantageously provides support for the prosthetic foot 100 when under a relatively high load. In some embodiments, the upper foot member 130 can be designed and/or selected for a particular amputee and/or activity so that the upper foot member 130 engages the intermediate foot member 120 under a specific load and provides a desired resistance to achieve a desired stiffness curve or performance for the foot 100. The upper foot member 130 can therefore provide for dynamic control under load.

The upper foot member 130 can have a split 138 near or along the longitudinal axis of the foot 100. The split 138 also can extend from the distal end 134 toward the proximal end 132 of the upper foot member 130. In some embodiments, the split can have a length of about 2 mm-10 mm in length. In some embodiments, the split does not extend proximate the base 170 of the ankle unit 160, but ends between the distal end 134 and the base 170. In some embodiments, the split can extend through the entire upper foot plate so that the upper foot plate is formed by a lateral portion and a medial portion. The lateral and medial portions can advantageously have different functional characteristics or appearances. As shown, the length of the split on the upper foot member can be varied for a particular amputee and/or activity so that a portion of the upper foot member near the distal end can flex somewhat independently, thereby providing a smoother rollover for the particular amputee and/or activity.

The lower foot member 110, intermediate foot member 120, and/or the optional upper foot member 130 can vary in length, width, and/or thickness, depending on the size of the prosthetic foot needed for the amputee. Accordingly, the stiffness of the combination of foot members can vary.

In some embodiments, the lower, intermediate, and/or upper foot members of the prosthetic foot of the present disclosure can have any other features described in U.S. application Ser. No. 15/139,047, filed Apr. 26, 2016, now U.S. Pat. No. 9,968,467, the entirety of which is incorporated herein by reference and is part of the disclosure. The embodiments described herein are compatible with and can be part of the embodiments described in U.S. application Ser. No. 15/139,047, and/or some or all of the features described herein can be used or otherwise combined together or with any of the features described in U.S. application Ser. No. 15/139,047.

Examples of Variable Stiffness Ankle Unit with a Single-Spring Design

Figure 2C:
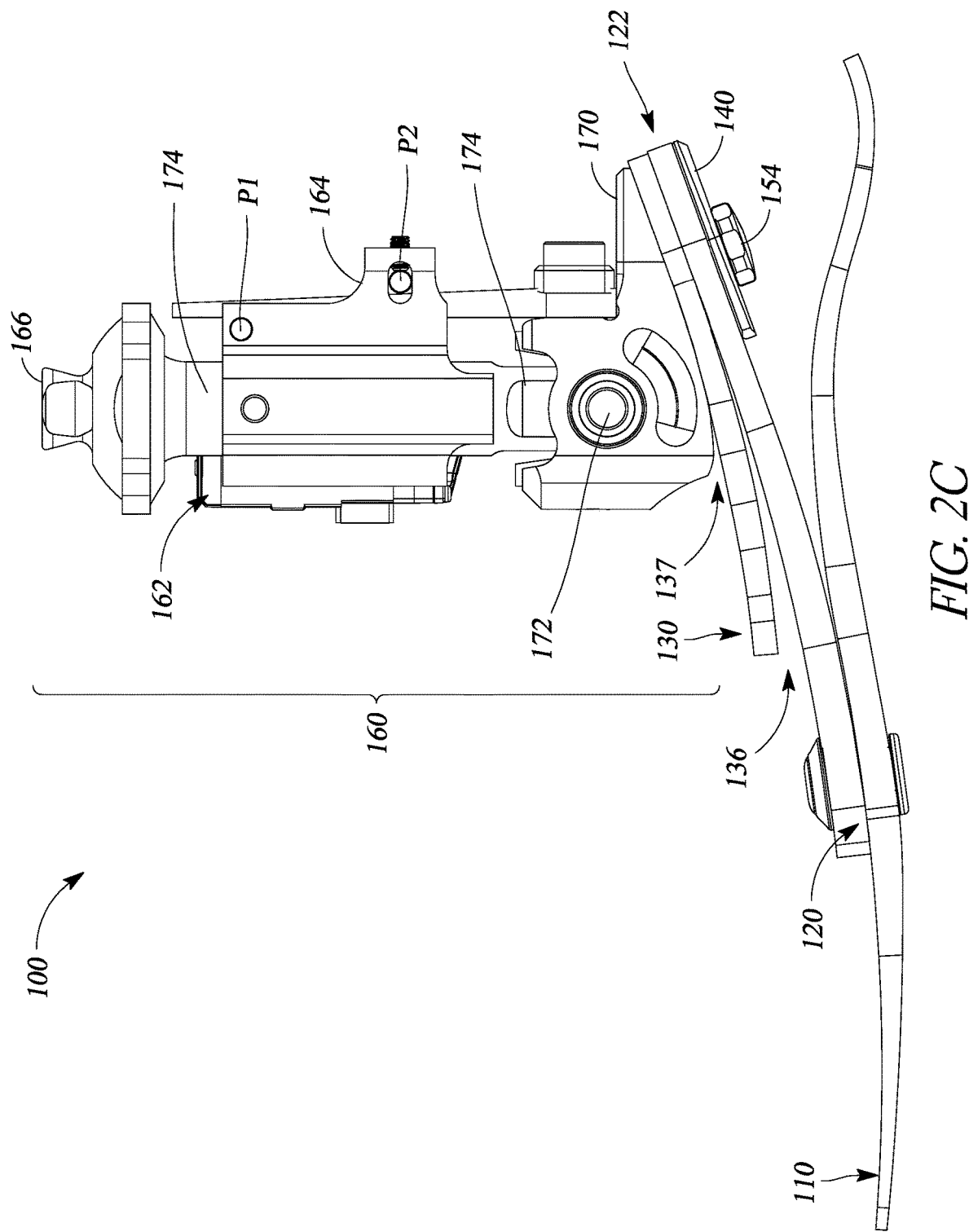
FIG. 2C illustrates a first side view of the prosthetic foot of FIG. 1A.
Figure 2D:
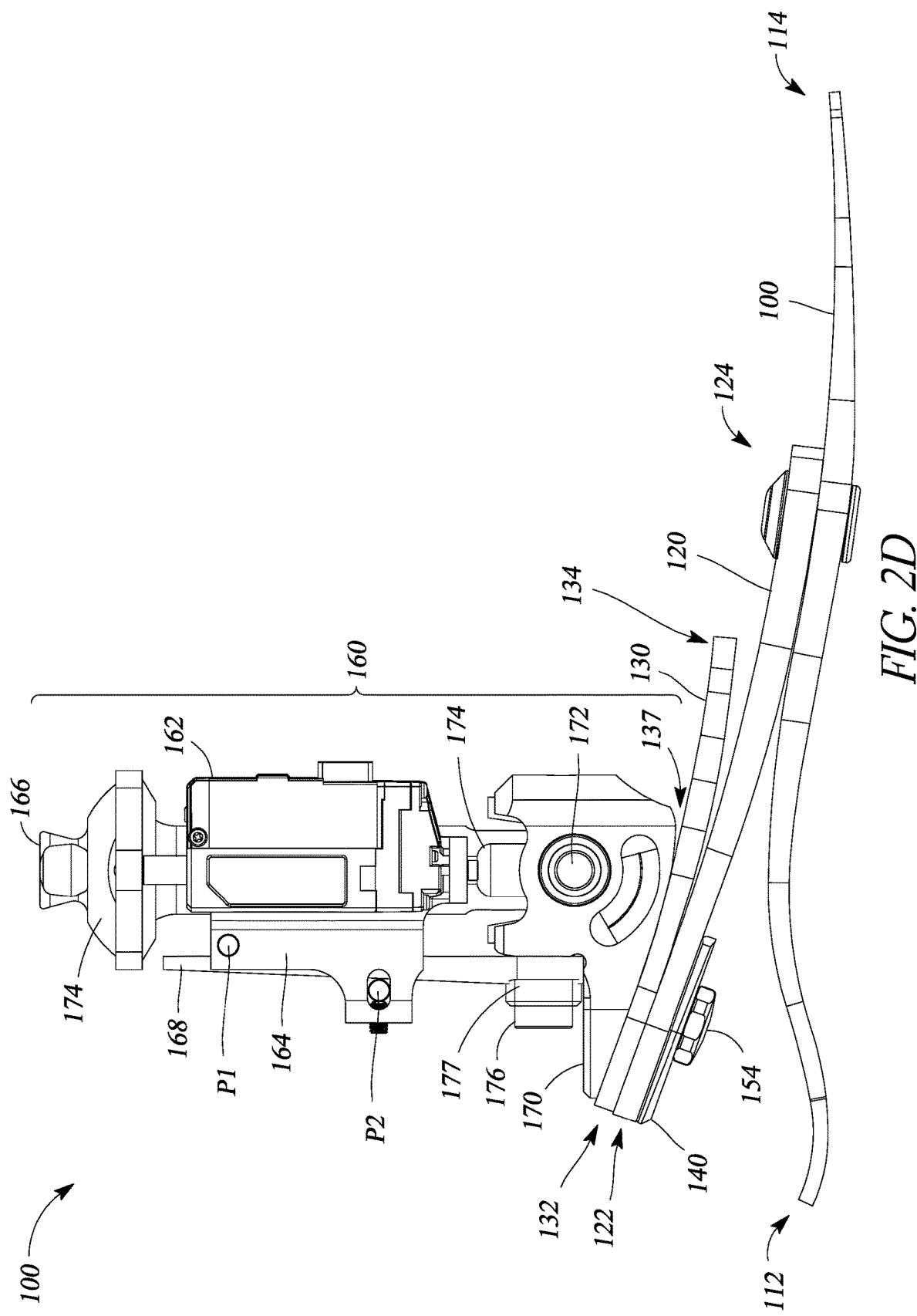
FIG. 2D illustrates a second side view of the prosthetic foot of FIG. 1A.
Figure 3:
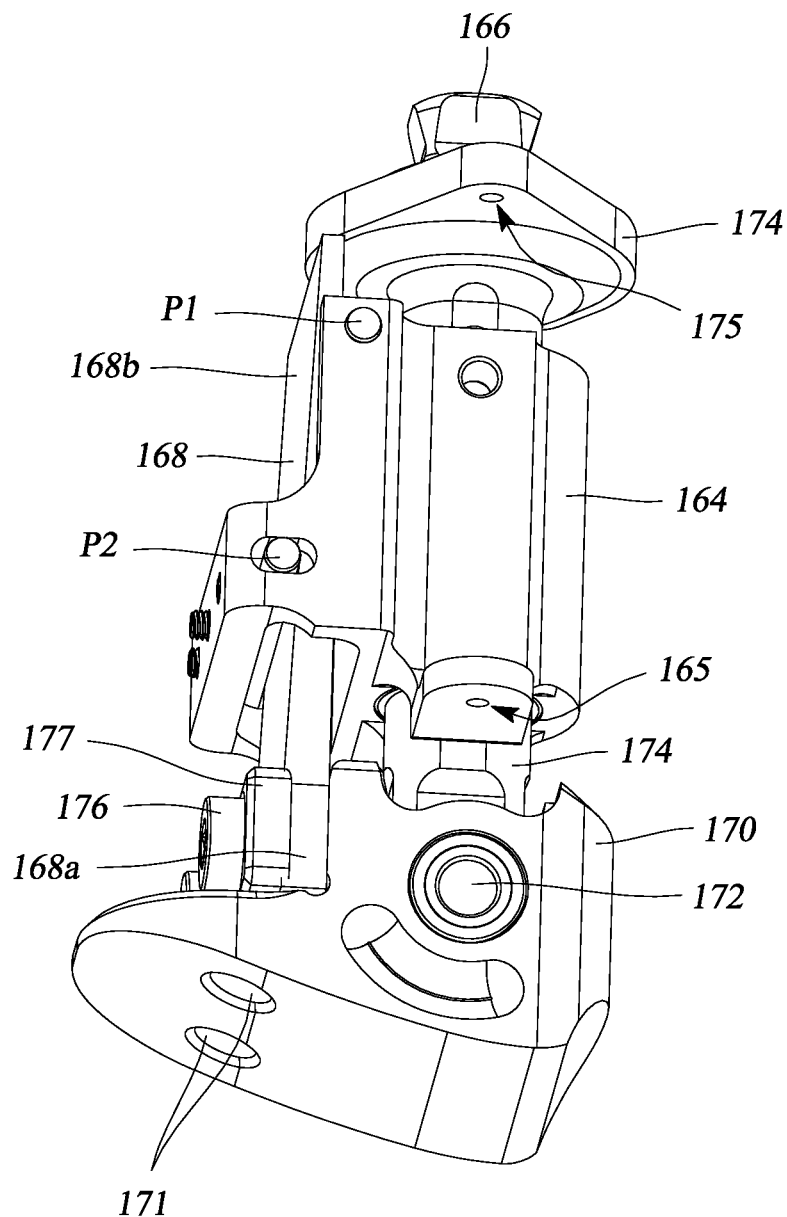
FIG. 3 illustrates a bottom perspective view of an example variable stiffness ankle unit of the prosthetic foot of FIG. 1A with the motor hidden for clarity.

Details of components of the variable stiffness ankle unit 160 of the prosthetic foot 100 will now be described. As shown in FIG. 3, the base 170 of the ankle unit 160 includes fastener holes 171. In some embodiments, the base 170 can be made from a relatively lightweight metal, for example, aerospace grade aluminum. As described above, the ankle unit 160 can be fastened to the intermediate foot member 120 (and optionally the upper foot member 130 and/or the shim 140) via connection between the base 170 and the intermediate foot member 120 (and optionally the upper foot member 130 and/or the shim 140). The base 170 and the intermediate foot member 120 (and optionally the upper foot member 130 and/or the shim 140) can be fastened via the fasteners 154 or otherwise. The base 170 can be placed relative to the intermediate foot member 120 (and optionally the upper foot member 130) such that an ankle pivot joint 172 of the base is at an approximate location of the anatomical ankle joint center of the amputee. A bottom surface of the base 170 can be curved. As shown in FIGS. 2C and 2D, the curvature on the bottom surface of the base 170 can result in a gap 137 at an anterior side between the ankle unit 160 and an upper surface of the upper foot member 130 (or the intermediate foot member 120 in a configuration that does not include the upper foot member 130). This gap 137 can allow the ankle unit 160 to roll up onto the upper foot member 130 or the intermediate foot member 120 as the foot 100 transitions from heel strike to toe-off, when the gap 137 closes, and the base 170 engages the upper foot member 130 or the intermediate foot member 120. This roll-up can increase the stiffness of the foot 100 as the foot 100 moves toward toe-off. In some embodiments, the gap 137 can gradually close, providing progressive stiffening of the foot during roll-up of the base 170 onto the foot member 120 or 130.

In the illustrated embodiments, the base 170 can be located at a distal end of the ankle unit 160. On a proximal end of the ankle unit 160, an adapter 166 can be configured to operably couple to a user's limb. In the illustrated embodiments, the adapter 166 can include a pyramid adapter. A generally vertical support beam or pylon 174 can extend between the adapter 166 and the base 170. In some embodiments, the pylon 174 can be made from a relatively lightweight metal, for example, aerospace grade aluminum. The pylon 174 can have a longitudinal axis that is configured to be oriented generally vertically when the prosthetic foot 100 is at rest (in a neutral position) on a level surface. A first end of the pylon 174 can be fixedly connected to the adapter 166. A second end of the pylon 174 can be rotatably coupled to the base 170 at the ankle pivot joint 172. The ankle pivot joint 172 can include a pin that extends along a width of the foot members 110, 120, 130 and/or the base 170. The ankle pivot joint 172 pin can be generally perpendicular to the sagittal plane S (in the anterior-posterior direction) of the prosthetic foot 100 so that the ankle unit 160 can rotate about the ankle pivot joint 172 along the sagittal plane. The ankle unit 160 can be rotated in a first direction so that the first end of the pylon 174 and/or the adapter 166 can rotate toward the heel end of the prosthetic foot in plantarflexion (see FIG. 5B, the longitudinal axis of the pylon as illustrated by the broken line rotating toward the heel end). The ankle unit 160 can be rotated in a second direction opposite the first direction so that the first end of the pylon 174 and/or the adapter 166 can rotate toward the toe end of the prosthetic foot in dorsiflexion (see FIG. 5C, the longitudinal axis of the pylon as illustrated by the broken line rotating toward the toe end).

Figure 5A:
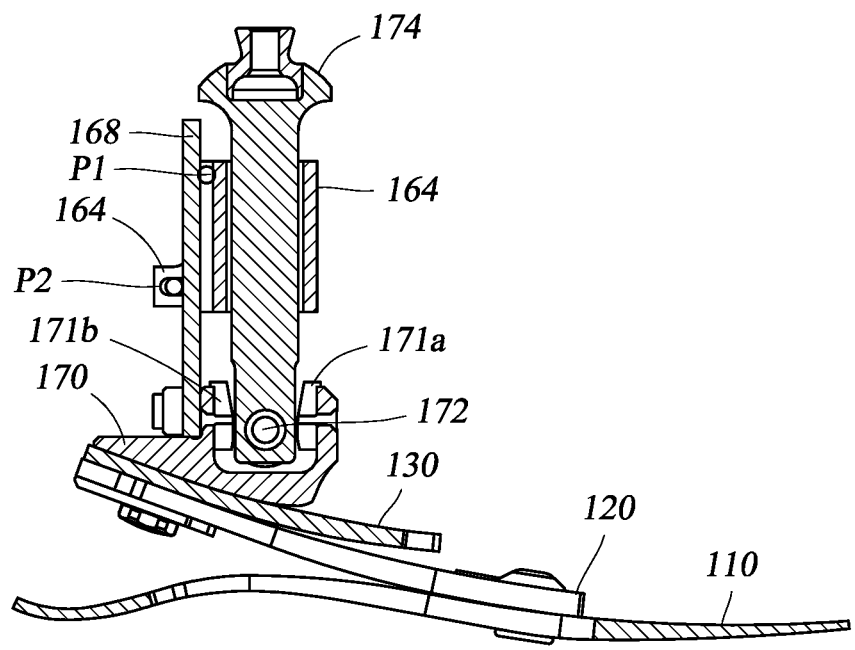
FIG. 5A illustrates a cross-sectional side view of an example prosthetic foot of the present disclosure (in a neutral position).
Figure 5B:
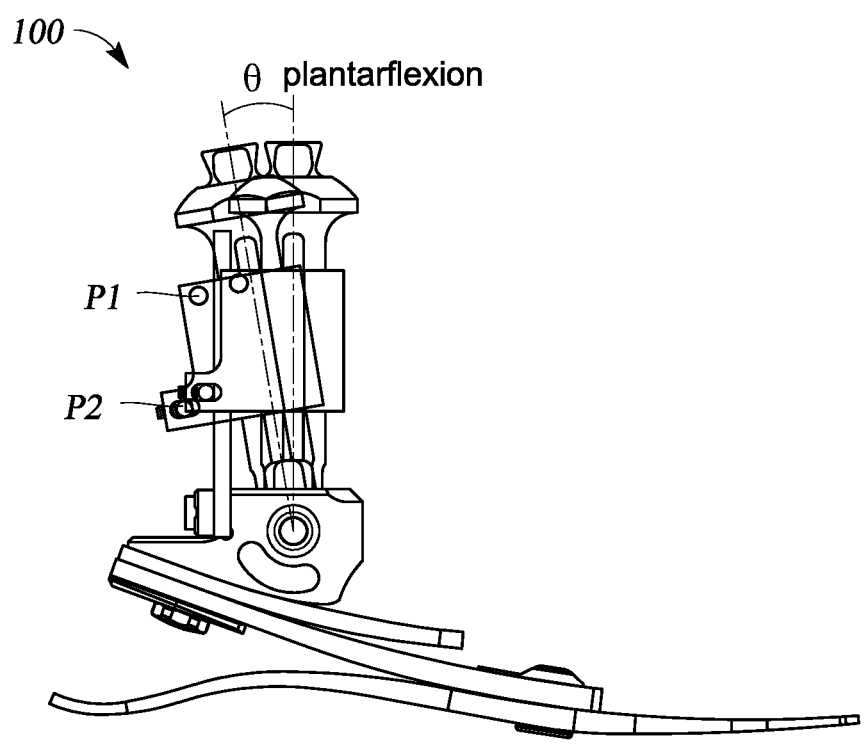
FIG. 5B illustrates a side view of an example prosthetic foot of the present disclosure in plantarflexion with the motor hidden for clarity.
Figure 5C:
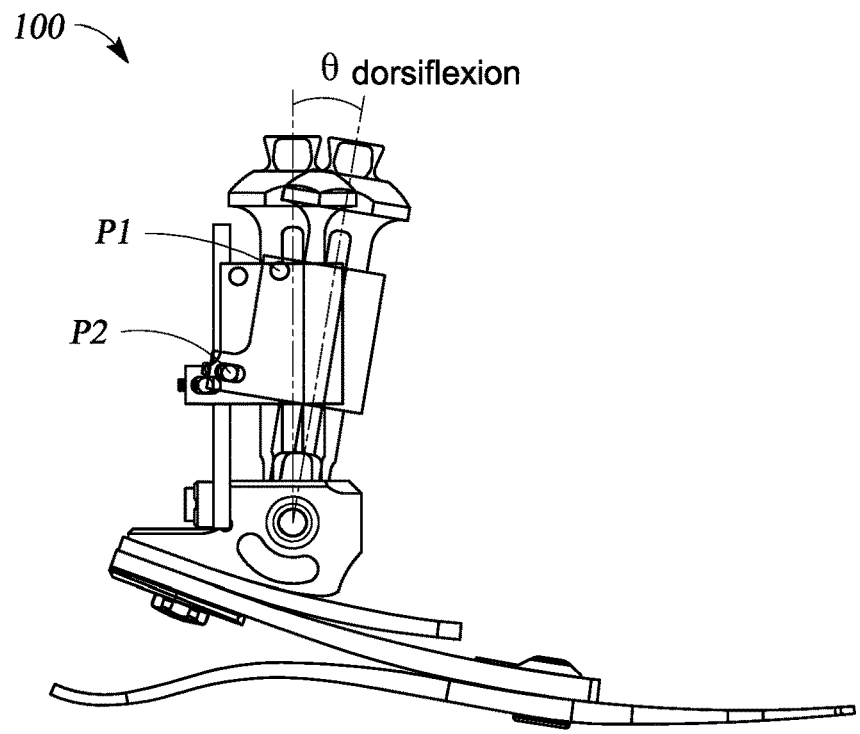
FIG. 5C illustrates a side view of an example prosthetic foot of the present disclosure in dorsiflexion with the motor hidden for clarity.
Figure 5D:
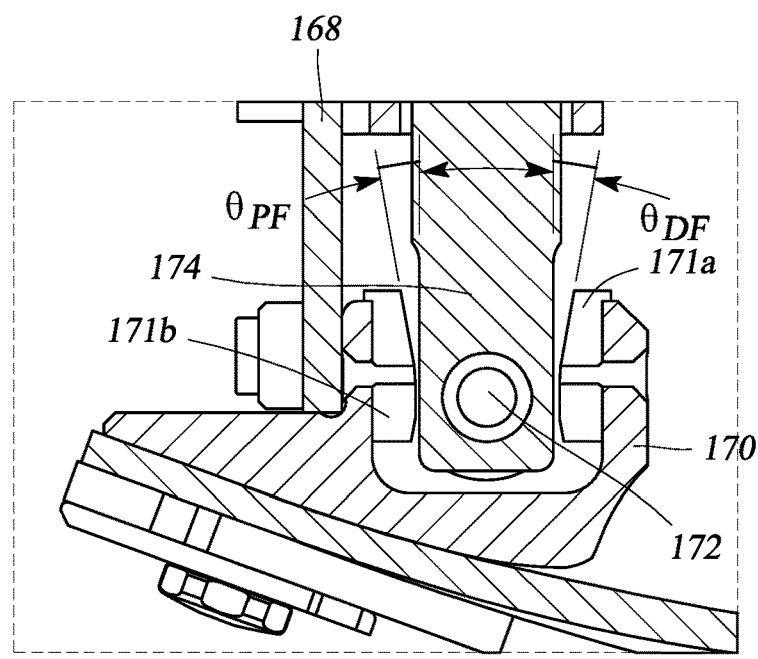
FIG. 5D illustrates a detailed cross-sectional view of an ankle pivot in an example prosthetic foot of the present disclosure.

As shown in FIGS. 5A and 5D, the base 170 can include wedges 171a, 171b with angled stopper surfaces facing the pylon 174 to stop the pylon 174 from further rotating in dorsiflexion and plantarflexion, respectively. In the illustrated embodiments, the wedges 171a, 171b can be fastened to an inner cavity of the base 170, which accommodates the second end of the pylon 174 pivotally connected to the ankle pivot joint 172 pin. In some embodiments such as shown in FIG. 5D, the ankle unit 160 is configured to dorsiflex up to an angle θDF in the range of about 7.5° to about 8.5°, or about 7.7° to about 8.3°, or about 8.0°. In some embodiments such as shown in FIG. 5D, the ankle unit 160 is configured to plantarflex up to an angle θPF in the range of about 9.5° to about 10.5°, or about 9.7° to about 10.3°, or about 10.0°. The angled stopper surfaces can be engaged during relatively high impact, which can stop one or more cantilever springs of the ankle unit 170 from carrying the full load and transmit a portion of the relatively high load to the one or more foot members 110, 120, 130. Accordingly, the angled stopper surfaces can combine the stiffness variation of the ankle unit 170 and the one or more foot members 110, 120, 130 of the prosthetic foot 100.

As shown in FIG. 3 (and also in FIGS. 1A, 2C, and 2D), the ankle unit 170 can include a cantilever spring 168. The spring 168 can be a leaf spring including a width (in the medial-lateral direction). As shown in FIG. 2A, the width of the spring 168 can be generally perpendicular to the sagittal plane S (in the anterior-posterior direction) of the prosthetic foot 100. In the illustrated embodiment, the spring 168 is located posterior to the pylon 174. Placing the spring 168 posterior to the pylon 174 can improve the appearance of the foot 100 and/or allow the ankle unit 160 to fit better in a calf volume than placing the spring in a different orientation relative to the pylon 174. In other embodiments, the spring can be located anterior to the pylon 174. In some embodiments, the spring 168 can be manufactured out of pre-impregnated S glass fibers (Mitsubishi composites, USA). As shown in FIG. 3, the spring 168 can include a first end 168a and a second end 168b along its length. The first end 168a can be fixedly connected to the base 170. In the illustrated embodiments, the first end 168a of the spring 168 can be clamped to the base 170 using a plurality of fasteners 176 extending through a plurality of fastener holes 169 in the spring 168 at or near the first end 168a. A washer 177 can optionally be included to more securely couple the first end 168a to the base 170. The second end 168b of the spring 168 can be a free end. The spring 168 can extend generally parallel to the longitudinal axis of the pylon 174. The second end 168b of the spring 168 can terminate below the first end of the pylon 174.

A body of spring 168 can engage a slider 164. In some embodiments, the slider 164 can be made from a relatively lightweight metal, for example, aerospace grade aluminum. In the illustrated embodiments of FIGS. 1A and 2A-3, the slider 164 can include a spring-engaging portion forming a first contact location P1 and a second contact location P2 for engaging the cantilever spring 168. P1 and P2 can be located between the first end 168a and the free second end 168b of the cantilever spring 168. Each of the contact locations P1 and P2 can include pins. The locations of P1 and P2 are also illustrated in FIG. 5A. As shown, the pins P1 and P2 can be on opposite sides of the spring 168 across its thickness. Accordingly, the reaction forces at P1 and P2 can act in opposite directions when P1 and P2 engage the spring 168, allowing two types of stiffness adjustment in the opposite directions. Cantilever beam principles can be applied. The deflection of the spring 168 under load can be converted to rotation about the ankle pivot joint 172. As shown in FIG. 5B, during plantarflexion (for example, during heel strike), P1 and P2 move toward the heel end of the prosthetic foot, resulting in the spring 168 being supported by P1 as the spring 168 that is also deflected toward the heel end and trying to return to its resting position is stopped by P1. In contrast, as shown in FIG. 5C, during dorsiflexion (for example, during toe off), P1 and P2 move toward the toe end of the prosthetic foot, resulting in the spring 168 being supported by P2 as the spring 168 that is also deflected toward the toe end and trying to return to its resting position is stopped by P2.

As P2 is closer to the base 170 than P1, the deflection of the spring 168 stores a greater force when the spring 168 is supported by P2 than by P1 (under the same moment, a shorter moment arm resulting in a greater force). P1 and P2 can therefore also allow for different stiffness values in opposite directions. This allows the prosthetic foot 100 to have a different stiffness in plantarflexion and dorsiflexion, with the stiffness in dorsiflexion (for example, during toe off) being higher than the stiffness in plantarflexion (for example, during heel strike). The distance between P1 and P2 on the slider 164 can generate a "gearing" or a defined ratio between the dorsiflexion stiffness and the plantarflexion stiffness when the stiffness is adjusted. In some examples, the dorsiflexion stiffness is about twice as the plantarflexion stiffness. In some examples, a vertical distance between P1 and P2 can range from about 30 mm to about 38 mm, or from about 32 mm to about 36 mm, or be about 34 mm. The ratio of the dorsiflexion stiffness and the plantarflexion stiffness can vary. In some embodiments, the difference in the dorsiflexion stiffness and the plantarflexion stiffness can vary based on other factors, for example, the type of foot members used, the need of the amputee, and/or otherwise.

Figure 6A:
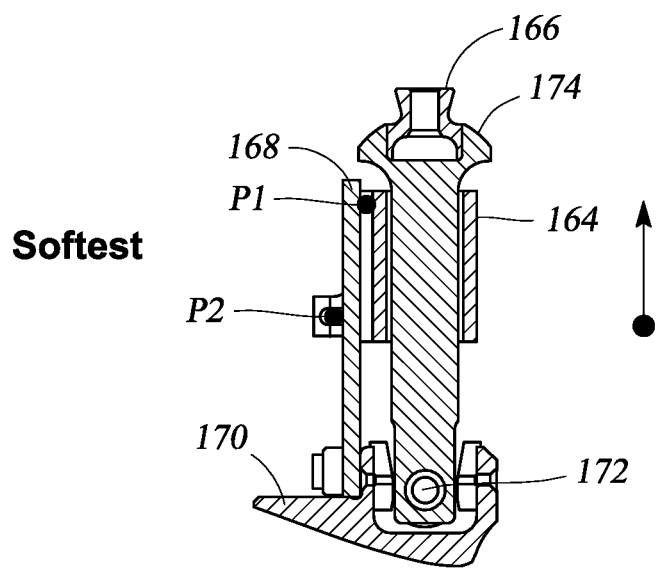
FIG. 6A illustrates a cross-sectional side view of an example variable stiffness ankle unit of the present disclosure with a lowest stiffness setting.
Figure 6B:
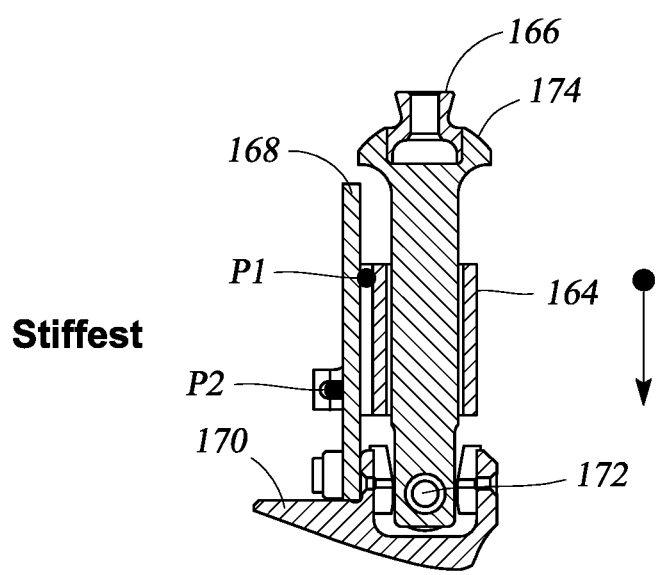
FIG. 6B illustrates a cross-sectional side view of an example variable stiffness ankle unit of the present disclosure with a highest stiffness setting.

The slider 164 can be configured to be movable relative to the longitudinal axis of the pylon 174 in response to a user input (such as via remote control using the user control device 200 as described above, or otherwise). The position of the slider 164 can be adjusted by translation relative to the longitudinal axis of the pylon 174 as shown in FIGS. 6A and 6B. In the illustrated embodiments, the slider 164 can include a pylon-engaging portion that extends circumferentially around the pylon 174 and is generally concentric to the pylon 174. In other embodiments, the pylon-engaging portion can have other configurations, for example, only partially extending around the circumference of the pylon 174. Translation of the pylon-engaging portion of the slider 164 along the length of the pylon 174 can simultaneously move the spring-engaging portion of the slider 164, thereby varying locations of P1 and P2, which varies a stiffness of the ankle unit 160 for both dorsiflexion and plantarflexion, while maintaining a higher stiffness for dorsiflexion than for plantarflexion. As shown in FIG. 6A, moving the slider 164 to be as close to the adapter 166 as possible results in the lowest stiffness of the ankle unit 160. As shown in FIG. 6B, moving the slider 164 to be as close to the ankle pivot joint 172 as possible results in the highest stiffness of the ankle unit 160.

In some embodiments, the slider movement can be automated by a motorized actuator or a motor 162, which can be wirelessly connected to the remote user control device 200 as described above. The electronic connection and communication between the motor 162 and the control system 190 has been described above. Mechanically, the motor 162 can be mounted between the slider 164 and the adapter 166 (or near the first end of the pylon 174) so that a shaft of the motor is generally parallel to the longitudinal axis of the pylon 174. As shown in FIG. 3, the pylon 174 can include an attachment location (such as an attachment hole 175) for connecting to one end of the motor 162 using a fastener, adhesive, friction fit, or otherwise. The slider 164 can include an attachment location (such as an attachment hole 165) for connecting to an opposite end of the motor 162 using a fastener, adhesive, friction fit, or otherwise. Accordingly, translation of a motor shaft of the motor 162 can translate the slider 164 toward or away from the adapter 162.

Optionally, as shown in FIGS. 4A and 4B (also in FIGS. 1A, 2C, 2D, and 3), the spring 168 disclosed herein can include a taper (for example, a linear taper) so that a thickness of the spring 168 increases (linearly) from the second free end 168b toward the first end 168a. In the illustrated embodiment, the taper can extend until a portion of the spring 168 near the first end 168a that generally overlaps with the washer 177. The portion of the spring 168 that generally overlaps with the washer 177 can have a generally uniform thickness, which can allow reduced stress where the spring 168 is fixedly connected to the base 170. In some embodiments, the taper can have an angle ranging from about 1.8° to about 2.8°, or from about 2.0° to about 2.5°, or about 2.3°. In one example, the thinnest portion of the spring 168 can be from about 2.5 mm to about 3.5 mm, or from about 2.7 mm to about 3.2 mm, about 3.0 mm. In one example, the thickest portion of the spring 168 can be from about 5.5 mm to about 6.5 mm, or from about 5.7 mm to about 6.2 mm, about 6.2 mm. The taper can allow a greater range of stiffness values than a spring with a uniform thickness when the slider 164 moves relative to the longitudinal axis of the pylon 174. Optionally, in addition or alternatively, the spring can include a taper in width (in the medial-lateral direction), which can further increase the range of stiffness values provided by the variable stiffness ankle unit. The dimensions (for example, in thickness and/or widths) and/or shapes (for example, tapered or non-tapered) of the cantilever spring can vary based on the choice of the foot members and/or on the amputee. In one example, the cantilever spring parameters can be selected to maintain a selected ratio of the dorsiflexion stiffness to the plantarflexion stiffness, such as about 2:1.

In some embodiments, the mechanical and weight bearing components of the ankle unit 160 can have a mass ranging from about 500 g to about 800 g, or from about 550 g to about 700 g, or about 600 grams. In some embodiments, the electronic components, that is, the control system 190 and the actuator 162, can have a mass ranging from about 200 g to about 350 g, or from about 240 g to about 300 g, or about 270 grams.

Working Examples of the Prosthetic Foot with a Single-Spring Design

The sagittal plane stiffness of example prosthetic feet of the present disclosure were measured with machine-based tests and compared to conventional biomechanical analysis using a human subject.

The plurality of foot members 110, 120, 130 and the variable stiffness ankle unit 160 can be considered to be connected in series. At least the stiffness of the foot members 110, 120 is fixed and can be selected according to existing stiffness categories available by the manufacturer (Össur PRO-FLEX® LP, 2020). The ankle unit 160 can be considered the foot's adjustable spring constant. The equivalent spring constant of the prosthetic foot 100 can be calculated as $1/k\_eq = 1/k\_foot\text{-}members + 1/k\_ankle\text{-}unit$, where k_eq is the equivalent spring constant, k_foot-members is the spring constant of the foot members, and k_ankle-unit is the ankle unit's spring constant.

Figure 7A:
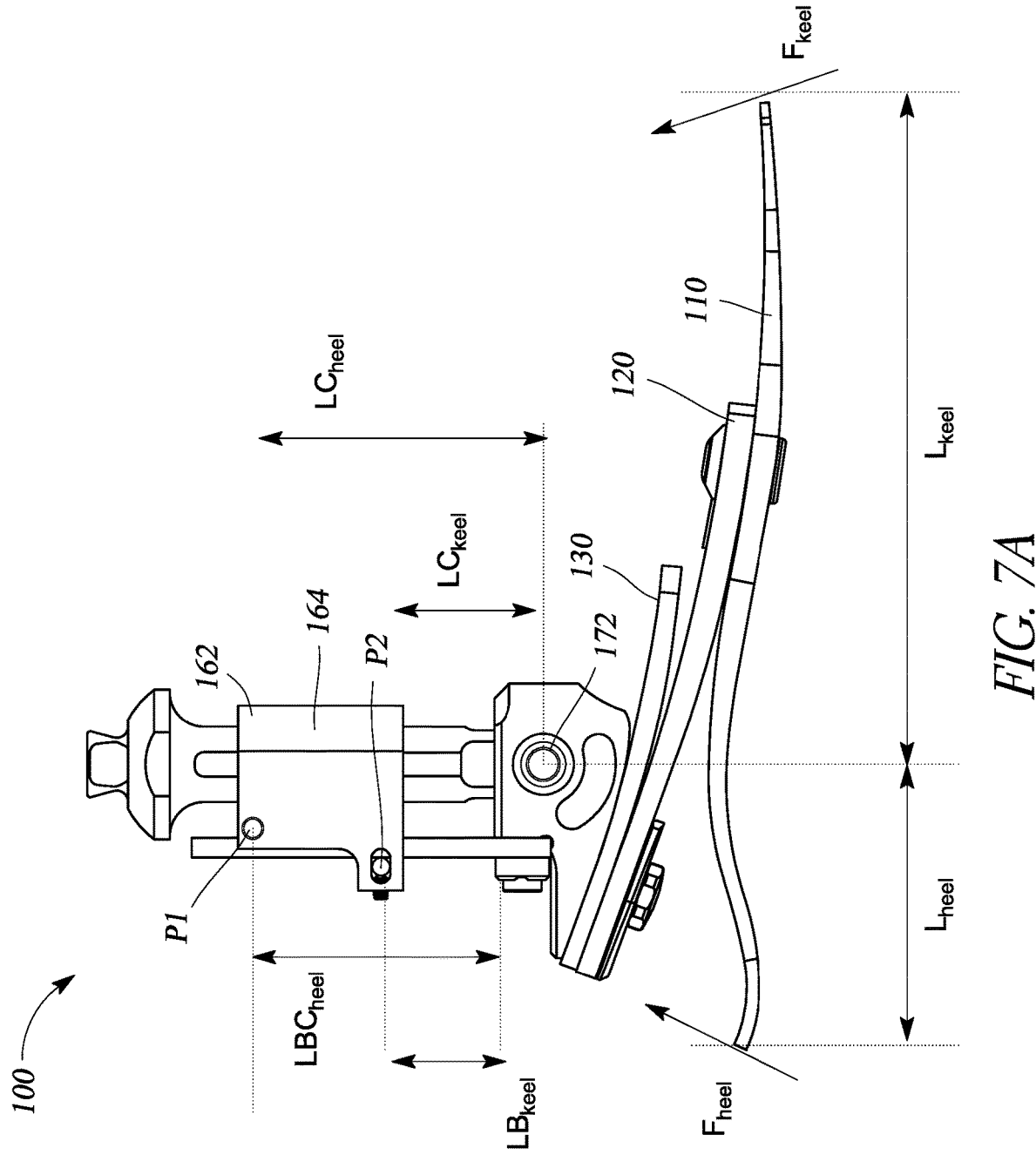
FIG. 7A illustrates schematically heel and keel (or toe) loads and definitions of certain mechanical parameters of an example prosthetic foot of the present disclosure.

As also described above, the contact locations P1 and P2 were positioned to reach higher ankle stiffness in dorsiflexion than in plantarflexion due to a lever arm ratio. The loads and moment arms along with geometrical aspects of the prosthetic foot 100 are shown in FIG. 7A. In FIG. 7A, LB indicates the lever arm length of the cantilever for the heel and the toe (also referred to as "keel"), and LC represents the length of the lever arm from P1 or P2 to the ankle pivot joint 172 for the heel and the toe respectively. The adjustable height of the slider 164 was primarily driven by the linear range of the actuator 162, which was a 25-mm span in this example. Width and thickness of the cantilever spring 168 were calculated to reach a stiffness change of 50% while remaining within acceptable stress of the material selected. As shown in FIG. 7B, for a foot size 27, the distance from P1 (the load application point or the contact point) to the ankle pivot joint 172 can be approximately 2.3 larger than the distance from P2 to the ankle pivot joint 172.

As described above, the deflection of the spring 168 translates to a rotational movement around the ankle pivot joint 172. A single-load cantilever beam deflection formula: $\partial = (FL^3)/3EI$ was applied in combination with the spring constant $k = 3EI/L^3$, where F is the force on P1 or P2 and $\partial$ is the deflection. Additional details of the parameters are listed in FIG. 7B. The deflection can be assessed by $\theta = \arctan(\partial/L\ support)$, where $\theta$ is the plantarflexion or dorsiflexion angle, $\partial$ is the deflection distance, and L support is the length of the lever arm. A MATLAB script was used to vary the inertia of the spring 168, the lever arm length and the stiffness of the one or more foot members 110, 120, 130. The range of motion of the prosthetic foot compared to an ESAR foot and the stiffness change resulted in a use of stiffer foot members in combination with the ankle unit were studied. To optimize the stress distribution in the spring 168, the thickness of the spring 168 was adapted to reach uniform stress.

Figures 8B, 8C:
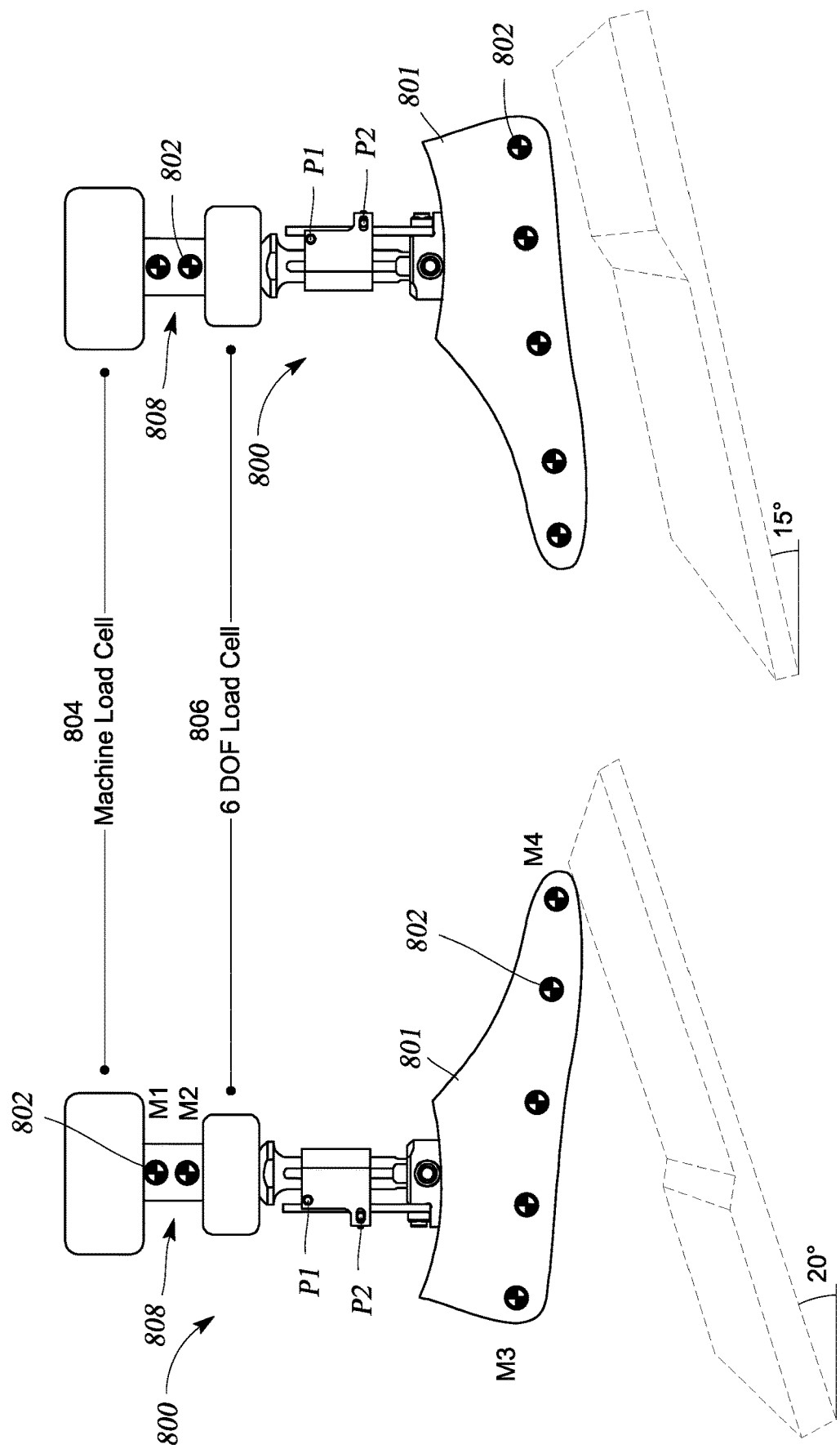
FIGS. 8B and 8C illustrate schematically a machine-based stiffness test set-up for testing the samples listed in FIG. 8A.
Figure 8D:
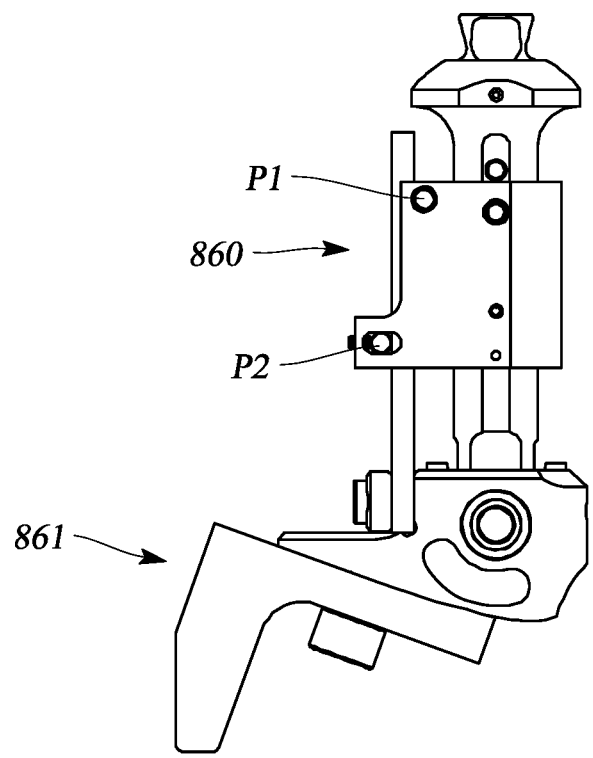
FIGS. 8D and 8E illustrate schematically rigid test fixtures used to test the variable stiffness ankle unit disclosed herein in machine-based testing.
Figure 8E:
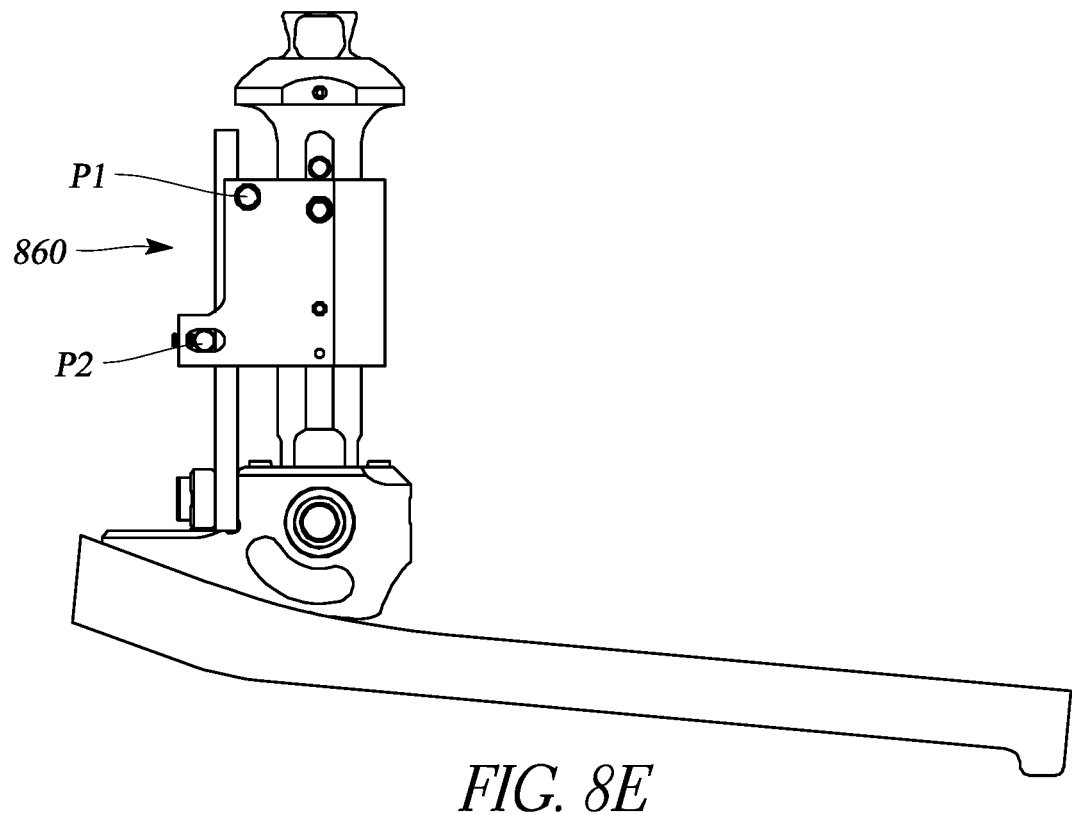

In machine-based (also referred to "static," "mechanical," or "experimental") tests, the prosthetic foot stiffness was characterized using a single-axis load compression test bench following AOPA guidelines for heel and keel (American Orthotic and Prosthetic Association, 2013). Heel and keel tests were performed through static compression using a compression machine 804 (Zwick, Switzerland) as shown in FIGS. 8B and 8C, with the load applied at constant speed (200 N/s). All samples tested are summarized in FIG. 8A. The following samples were tested: variable stiffness ankle unit only samples 860, ESAR Foot (cat 5 size 27) only samples, and a combination of ESAR foot members assembled with the ankle unit (that is, variable stiffness foot samples 800). The AOPA test set-up for the variable stiffness foot shown in FIGS. 8B-C, with FIG. 8B illustrating a toe stiffness test (dorsiflexion) and FIG. 8C illustrating a heel stiffness test (plantarflexion). For the ankle unit only samples 860, rigid fixtures 861, 862 shown in FIGS. 8D and 8E were mounted for plantarflexion in a heel test (FIG. 8D) and dorsiflexion in a keel test (FIG. 8E) to evaluate performance of the ankle unit solely samples 860. Load application points (that is, positions of P1 and P2) were kept identical for the foot size tested to keep the lever arms constant. The variable stiffness ankle unit 860 was tested for three stiffness settings, from the maximum to minimum possible positions of the slider (that is, the positions of P1 and P2). Positions of the slider for the softest setting were LCkeel=53 mm and LCheel=87 mm. Positions of the slider for the mid setting were LCkeel=43 mm and LCheel=77 mm. Positions of the slider for the stiffest setting were LCkeel=33 mm and LCheel=67 mm.

As shown in FIGS. 8B and 8C, to further characterize the stiffness of the variable stiffness prosthetic foot samples 800, a six-degree of freedom load ("6-DoF") cell 806 (Sensix, France) was added at the proximal connection of the samples tested. The six-degrees of freedom load cell 806 was used in conjunction with a 2D camera (not shown) to provide information on the samples' mechanical properties in the sagittal plane. This method was used to collect comparable data between the machine-based test and conventional biomechanical analysis. Sagittal plane movements were recorded using a video camera (GoPro Hero 5, USA) while tests were performed using the compression machine 804. Plantarflexion and dorsiflexion ankle stiffness was calculated using the heel and keel AOPA tests described above. As shown in FIGS. 8B and 8C, the six-degree of freedom load cell 806, installed proximally to the prosthetic foot samples, allowed collection of force and moment data in the three planes. Seven markers 802 were placed on a cosmetic foot shell 801 of the prosthetic foot sample 800 and a rigid connector 808 to allow tracking of the ankle motion. Sagittal foot movements was recorded with the video camera at 25 Hz. The machine-based tests were performed with the cosmetic foot shell 801 but without shoes.

A baseline test was first conducted on an ESAR foot (Pro-Flex LP, Össur, Iceland) category 5 size 27. The ankle unit only sample 860 was then assessed at the three different positions of the slider. Lastly, the variable stiffness prosthetic foot sample 800 was tested at the same three slider positions. A load of 1200 N was applied at a constant speed for the ESAR foot sample and the variable stiffness prosthetic foot sample 800, and a load of 900 N was applied for the ankle unit only sample 860.

Stiffness was calculated at a slope between 10% and 100% of the load value. The angular stiffness modulus $k\_\theta$ can be calculated using the formula: $k\_\theta = M\_(\text{Load Cell})/(\theta\_(\text{Ankle Angle}))$, where $k\_\theta$ is the rotational stiffness calculated at the ankle pivot joint 172 for plantarflexion during a heel test and dorsiflexion during a keel test. The moment $M\_(\text{Load Cell})$ is recorded in the sagittal plane. $\theta\_(\text{Ankle Angle})$ is the plantarflexion or dorsiflexion angle between approximately the lower foot member and the pylon, which can be tracked using the marker-defined segments M1-M2 (pylon) and M3-M4 (approximately the lower foot member) respectively (see FIG. 8B).

For conventional biomechanical analysis, a pilot study was performed to evaluate user perception and biomechanical effects of the stiffness change. One male transtibial amputee (age: 50, height: 1.78 m, weight: 100 kg, time since amputation: 12 years, current prosthetic foot: PRO-FLEX® Pivot, Össur, Iceland) participated in the study. The biomechanical study was approved by the Icelandic national bioethics committee, and the subject gave an informed consent prior to testing.

Prior to the biomechanical data collection, the same version of the variable stiffness prosthetic foot as used in the machine-based tests was tested without failures for 100 000 cycles according to ISO 10328:2016. The test was performed to lower potential residual risks when performing the subject trial.

The variable stiffness prosthetic foot was aligned at the mid stiffness setting, by an experienced certified prosthetist and alignment pictures were recorded using an L.A.S.A.R posture (Ottobock, Germany). The variable stiffness prosthetic foot was aligned and tested with a sport shoe (Viking). The foot tested was the only alteration from the subject's daily prosthesis.

The biomechanical study was conducted on an instrumented split-belt treadmill (Bertec, USA). Motion was recorded using an 8-camera Qualisys system (Qualisys, Sweden) and ground reaction forces were acquired by the two treadmill force plates, both at 400 Hz. Marker setup was in accordance with the 6-DoF model described above. The subject walked at a self-selected speed at 0° elevation (1.0 m/s), on three different stiffness settings, for approximately 2 minutes in each setting. Accommodation time preceded each stiffness change, varying from 5-15 minutes or enough for the subject to be comfortable with each setting. The three stiffness settings were tested randomly and blinded for the subject. Lower-body kinematics and inverse dynamics were processed using Visual 3D software (C-Motion, USA).

Figure 9A:
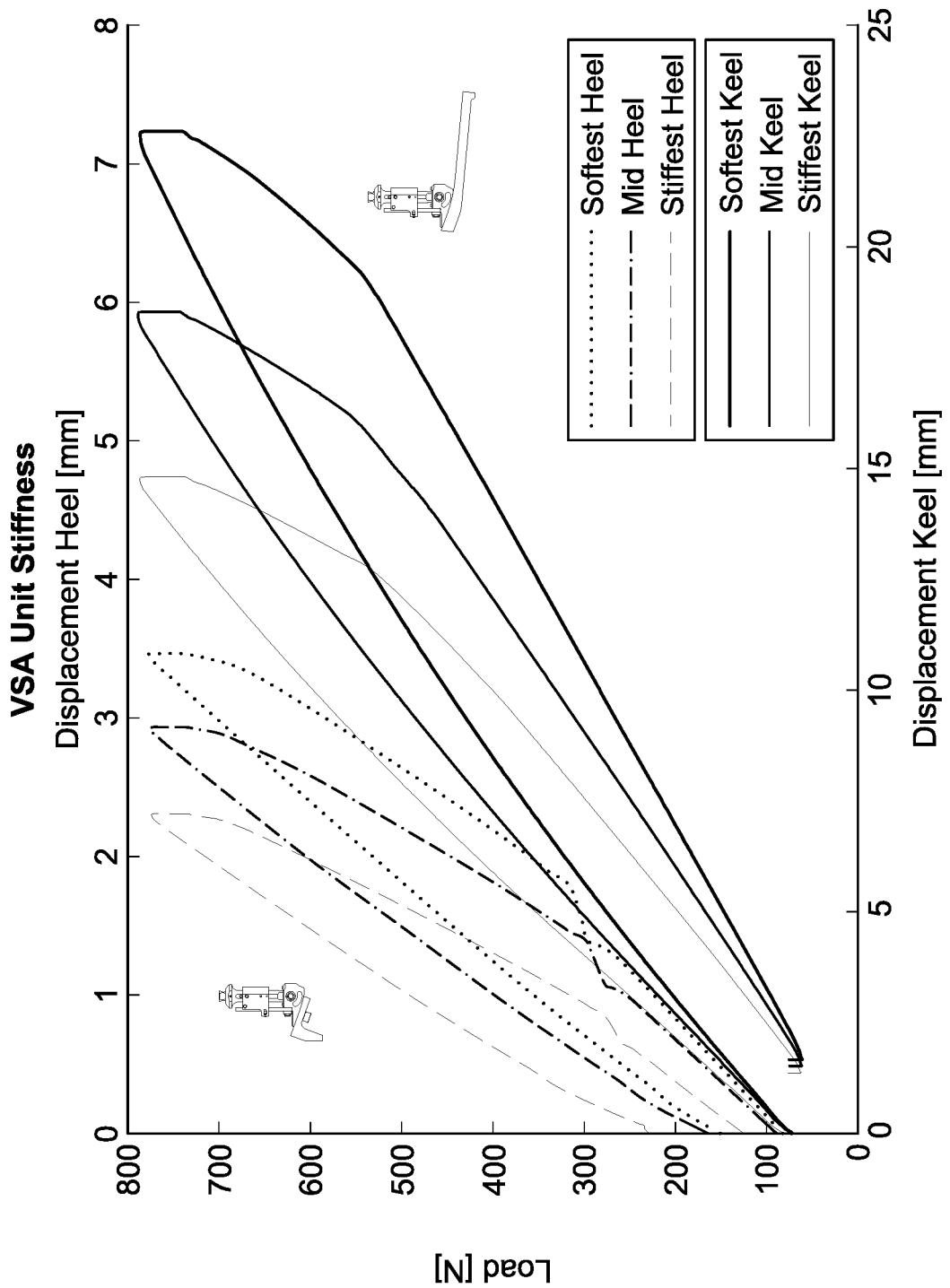
FIGS. 9A-9D are graphs results of the machine-based tests illustrated in FIGS. 8A-8E and a biomechanical study on a human subject.

Results of the machine-based tests and the biomechanical study will now be described. FIG. 9A illustrates for the heel (broken lines) and the keel (solid lines), the ankle unit load versus displacement for the three stiffness settings. As shown in FIG. 9A, the stiffness of the ankle unit for both the heel and the keel showed a clear difference between the three stiffness settings during the static machine-based tests. The ankle unit measured a 25% increase in displacement from the softest to the mid-stiffness setting and a 48% to 51% increase in displacement from the softest to the stiffest setting. However, the static tests on the ankle unit presented some hysteresis as shown above in FIG. 9A. A flat step was seen for the heel test during unloading in the softest position, which was not present for the keel test. The friction of the soleus blade on the carrier may have caused this plateau in the curve. Accordingly, some embodiments, friction in the prosthetic foot may be adjusted to lower the hysteresis.

Figure 9B:
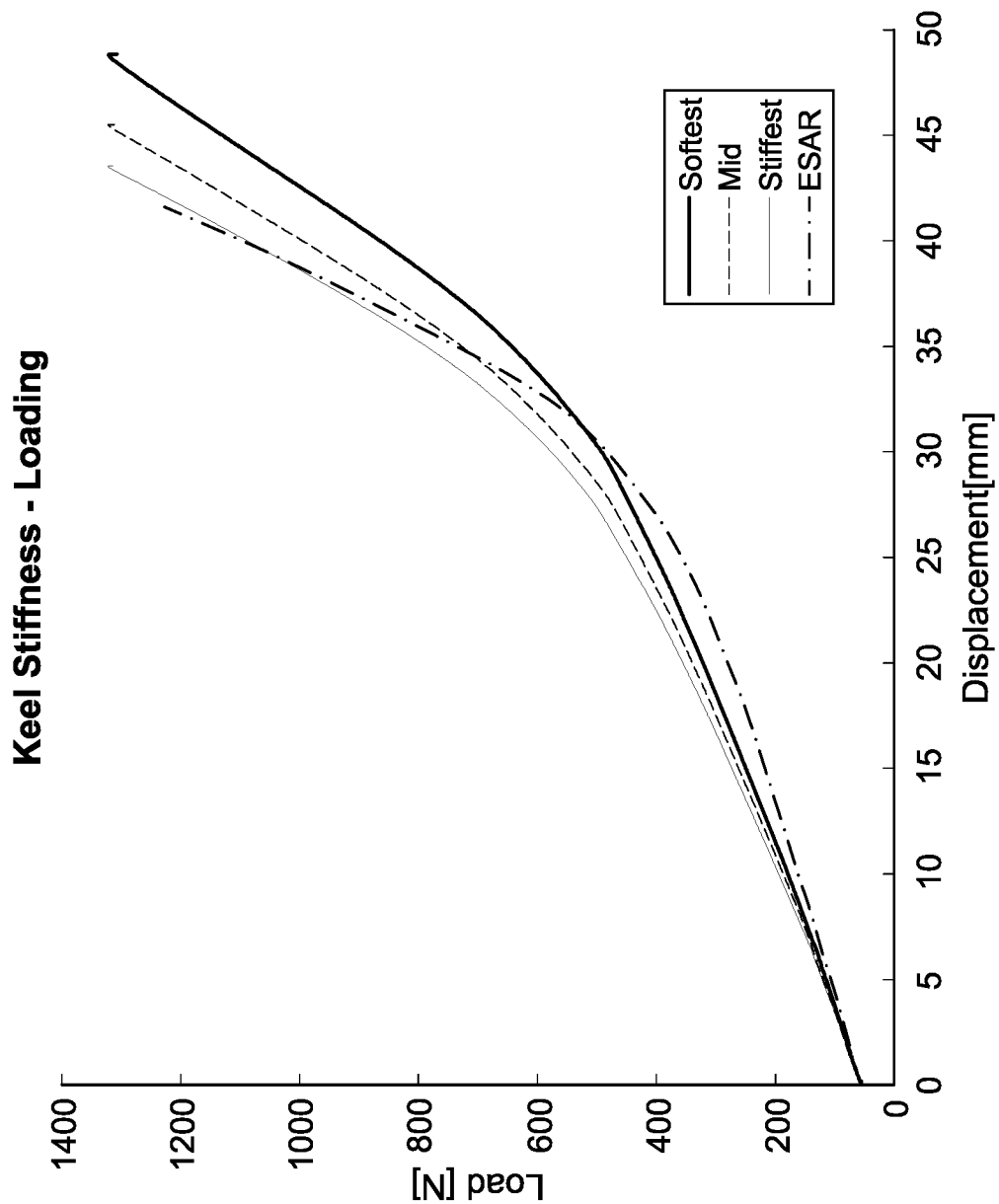

As noted above, the stiffness of the variable stiffness foot sample was measured for the same three settings. The keel stiffness results (solid lines) of the variable stiffness foot are shown and compared with the keel loading results (broken lines) of the commercially available ESAR foot in FIG. 9B.

Figure 9C:
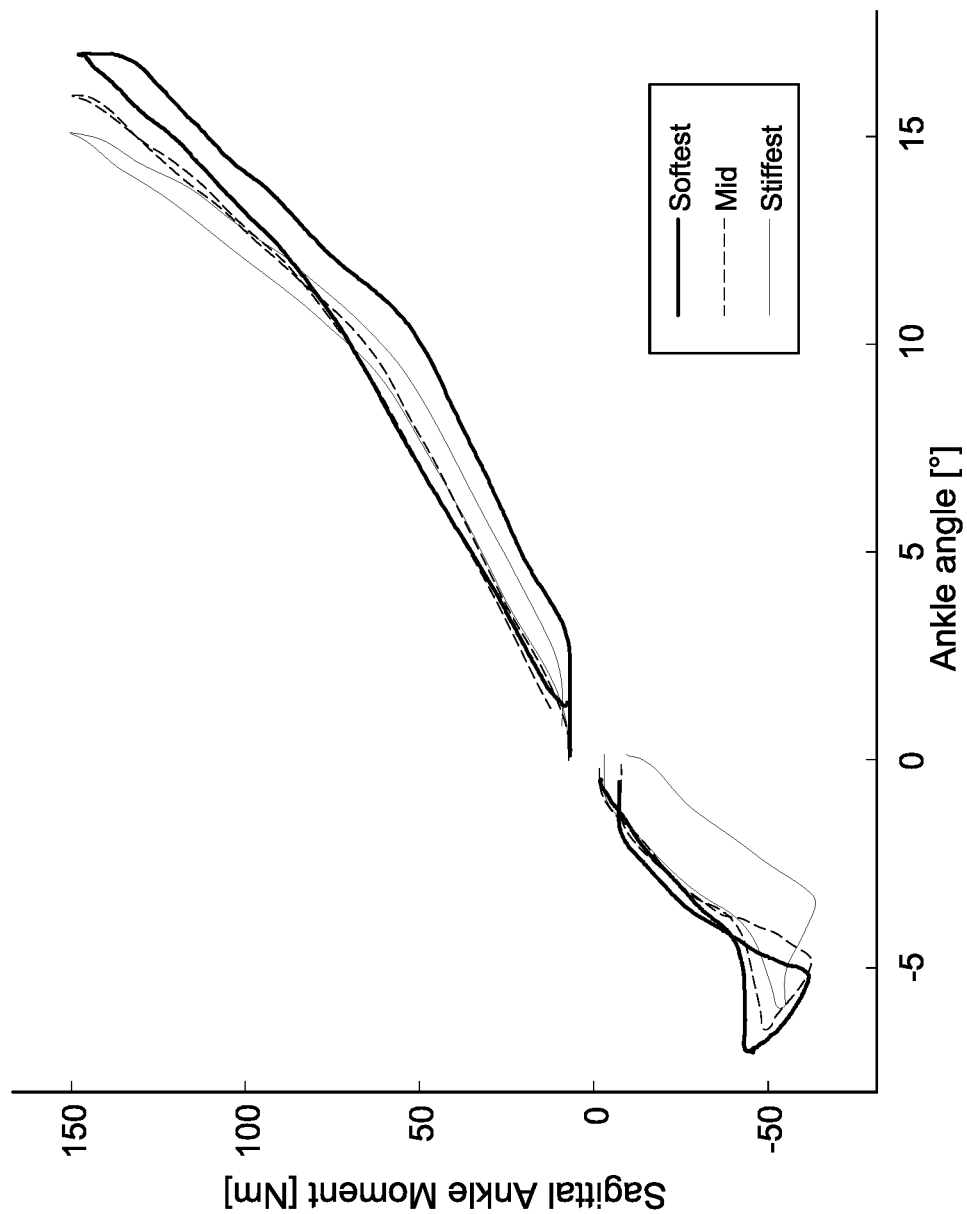
Figure 9D:
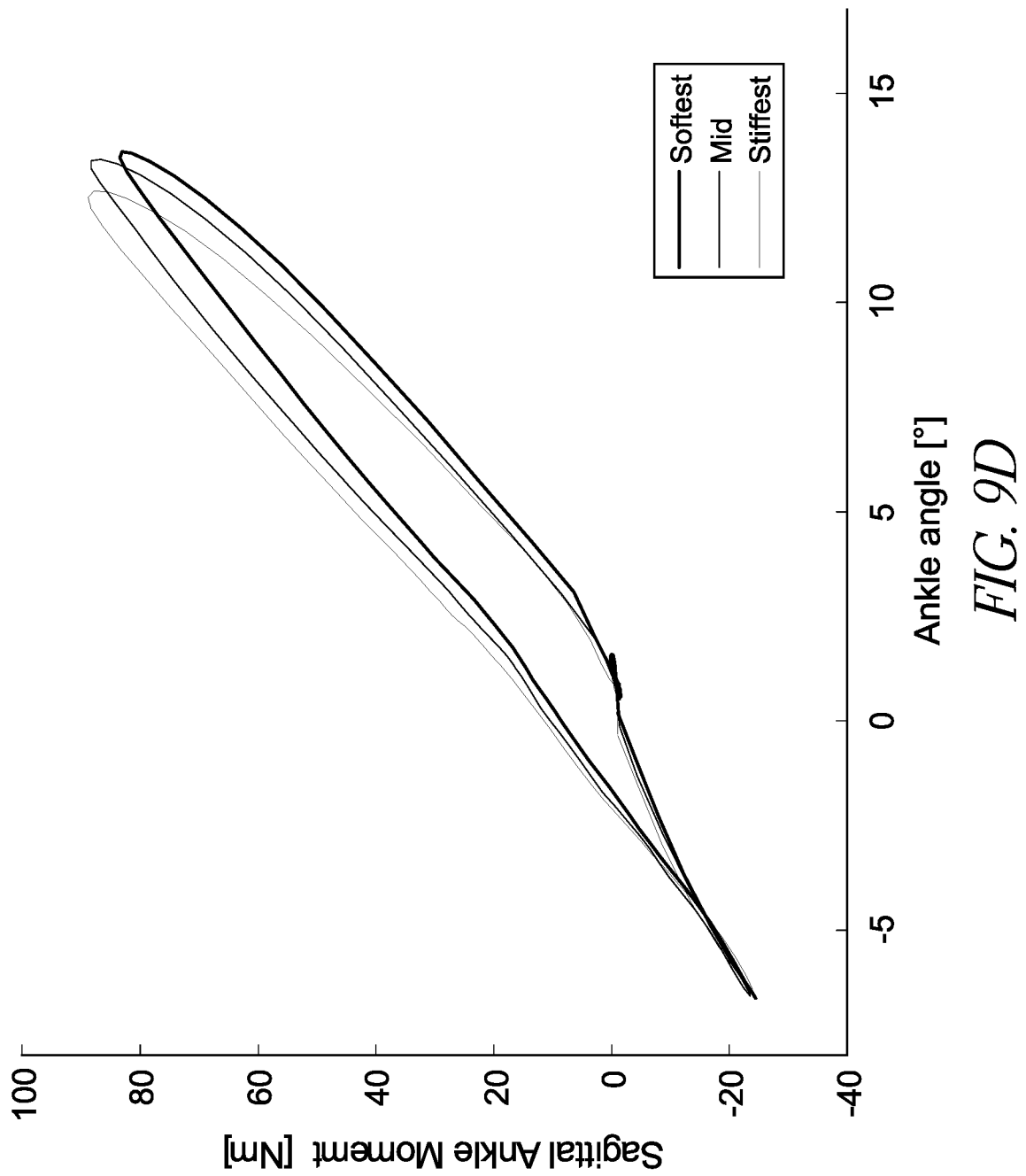
Figure 12A:
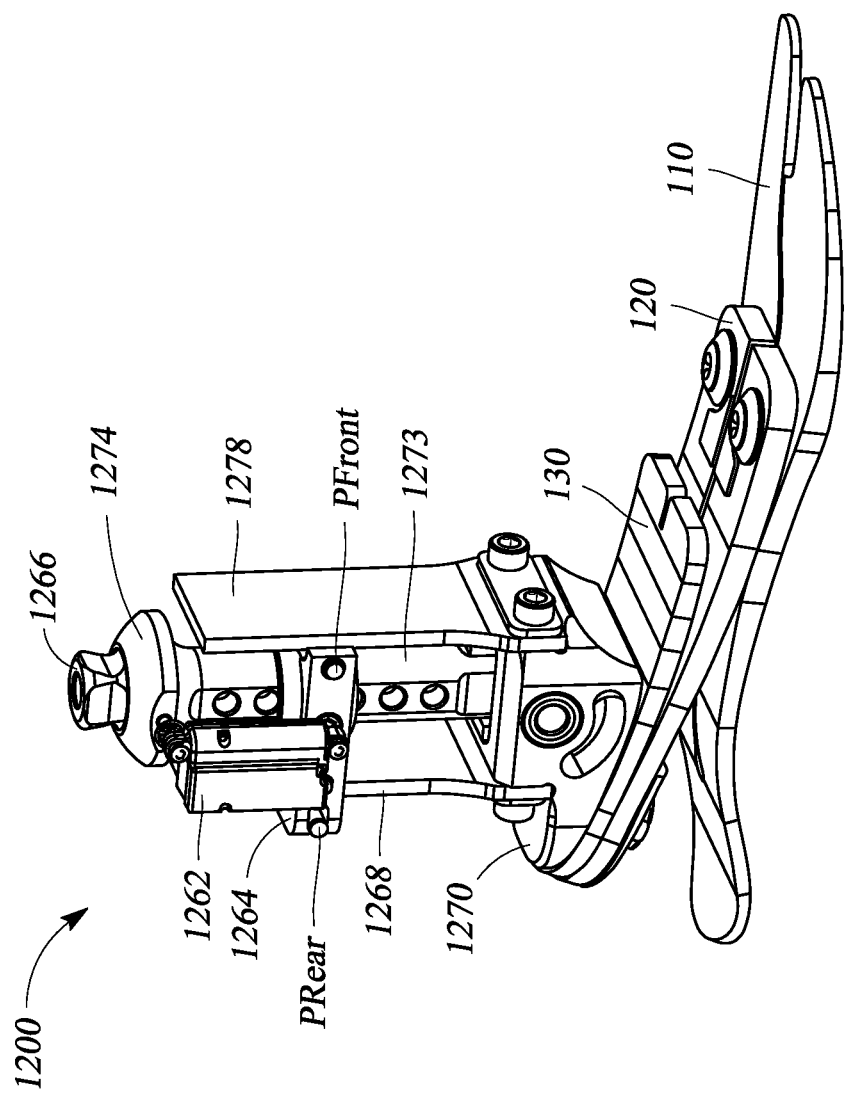
FIG. 12A illustrates a perspective view of a prosthetic foot with another example variable stiffness ankle unit.
Figure 12B:
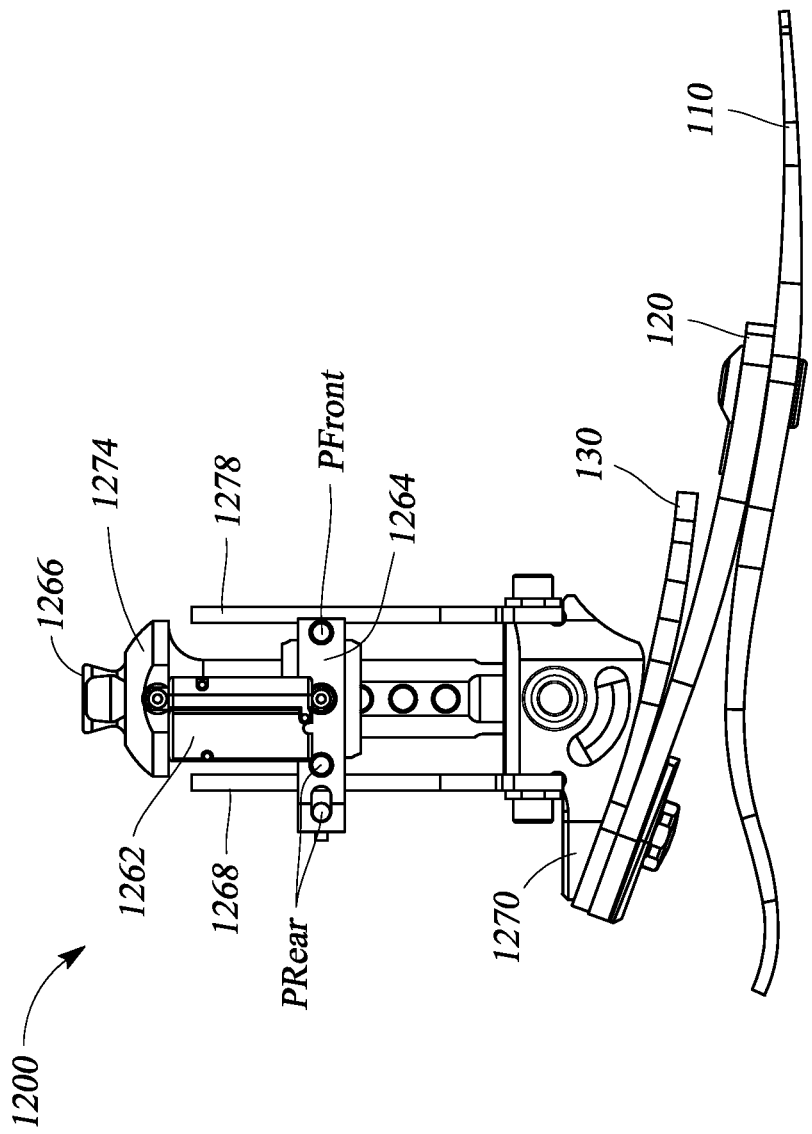
FIG. 12B illustrates a side view of the prosthetic foot of FIG. 12A.

The machine-based test results were contrasted with biomechanical results during level ground gait by the subject in the pilot study. FIGS. 9C and 9D present the average sagittal ankle moments versus the ankle angle under the three different stiffness settings. FIG. 9C illustrates the machine testing results at a load of 1250 N. As noted above, when performing the AOPA stiffness tests, the set-up shown in FIGS. 8B and 8C allowed for the capture of additional information with the 6-DoF load cell and the camera. The ankle moment and angle properties of the variable stiffness prosthetic foot were derived by syncing the signal of the 6-DoF load cell and the foot motion in the sagittal plane captured by the camera. The measured ankle moment versus ankle angle during the machine-based test of the variable stiffness foot sample is shown in FIG. 9C. The ankle angle decreased with increased stiffness settings for both plantarflexion and dorsiflexion. FIG. 9D illustrates the biomechanical study results when the subject walked on level ground for 2 minutes. As shown in FIG. 9D, the dorsiflexion ankle angle decreased with higher stiffness settings of the variable stiffness prosthetic foot during the biomechanical study. The pilot test subject was able to perceive the different stiffness settings despite being blinded to each stiffness condition, and reported changes in the prosthetic foot rollover with each stiffness adjustment.

A finite element model (FEM) of an example prosthetic foot of the present disclosure was created in Solidworks (3DS, France) to evaluate the change of the prosthetic foot angular stiffness depending of the slider position. The model was set-up to reproduce the machine-based heel and keel tests from the AOPA guidelines, and a load of 1200 N was applied to the heel and the keel, respectively. The metal parts of the prosthetic foot were modelled as rigid, whereas the foot member composites parts and the cantilever spring were defined as flexible bodies. Thickness of the foot member composite parts were calculated from the laminate's layup schedules. The Young's modulus of the carbon fiber was set to 97 GPa and the S-glass fibers to 50 GPa in the fiber direction based on three-point bending tests previously conducted. Contact surfaces were defined for the foot members and P1 and P2 sliding on the spring. A pivot connection was used between the base of the ankle unit and the pylon allowing rotation under deflection of the spring. Friction coefficient of 0.3 was used between a load application plate and contact surfaces to ESAR foot while frictionless contacts were defined for the variable stiffness prosthetic foot. Since large deformation are occurring in the composite foot members, a large displacement solver was selected.

FIG. 10A illustrates an FEM of the variable stiffness prosthetic foot in dorsiflexion (keel stiffness test) and FIG. 10B illustrates an FEM of the variable stiffness prosthetic foot in plantarflexion (heel stiffness test). The ankle angle was measured between the lower foot member and the pylon using the deformed shape for the heel and keel test model results. FIG. 10C compares the experimental data from the machine-based tests and the FEM under the three different stiffness settings. The FEM predicted the change of angular stiffness for each position of the slider in a manner consistent with the machine-based tests.

Angular stiffness and the stiffness change percentage for each setting of the variable stiffness foot are shown in FIG. 11. The table in FIG. 11 summarizes plantarflexion and dorsiflexion stiffness and the calculated stiffness change percentage for the FEM, the machine-based tests, and the biomechanical study under the three different stiffness settings. The FEM results were consistent with the machine-based testing. Results of the biomechanical analysis showed clear differences in the ankle angle/moment values during level ground walking under the three stiffness settings.

Although the dorsiflexion stiffness change between the machine-based tests and the biomechanical study followed a similar trend, the data also demonstrated some conflicting results. The angular stiffness change was comparable between the three settings of the variable stiffness prosthetic foot. However, the angular stiffness modulus was typically lower for the biomechanical analysis compared to the experimental machine-based tests. The lower modulus for dorsi- and plantarflexion reported from this biomechanical study may be due to the large difference in a dynamic bipedal gait pattern compared to the static load applications of the machine-based tests.

The biomechanical study results for plantarflexion stiffness changes during level ground gait were minor, whereas clearer differences were seen in the machine-based test results. This may reflect differences in the test set-up, as the machine-based testing was performed as two distinct static tests where loads were applied on the keel and heel while the biomechanical outcomes are derived from a single dynamic roll-over motion. Furthermore, the machine-based test was performed without shoes while the biomechanical study was performed with shoes. The softer heel cushioning of the shoes might have had an impact on the test results during plantarflexion. The limited stiffness variation for plantarflexion recorded during gait analysis did not relate to the subject's perception. As noted above, the subject reported alteration of the foot response from heel-strike to toe-off affecting the prosthetic foot roll-over.

Other Examples of a Variable Stiffness Ankle Unit

In some embodiments, such as shown in FIGS. 12A-12B and 13A-13B, a prosthetic foot 1200, 1300 can include a first cantilever spring 1268, 1368 and a second cantilever spring 1278, 1378. The first cantilever spring 1268, 1368 and the second cantilever spring 1278, 1378 can have any of the features of the cantilever spring 168 described above. The prosthetic foot 1200, 1300 and any of its components other than the cantilever springs, including the slider 1264, 1364, the pylon 1274, 1374, the base 1270, 1370, the foot members 110, 120, 130, the motor 1262, and the adapter 1262, 1362 can incorporate any of the features of the prosthetic foot 100 and its components described above. The prosthetic foot 100 and its components can likewise incorporate any features of the prosthetic foot 1200, 1300.

In FIGS. 12A-12B and 13A-13B, the first spring 1268, 1368 can be located rearward of the pylon 1274, 1374 and the second spring 1278, 1378 can be located forward of the pylon 1274, 1374. The slider 1264, 1364 can include a first contact location $P_{Rear}$ for the first spring 1268, 1368 and a second contact location $P_{Front}$ for the second spring 1278, 1378. Accordingly, translation of the slider 1264, 1364 along the length of the pylon 1274, 1374 can adjust stiffness of the foot 1200, 1300 in the sagittal plane of the foot. As shown, the first contact location $P_{Rear}$ can extend around both the front and rear sides of the first spring 1268, 1368. Regardless of the direction of deflection, the first spring 1268, 1368 can receive a load from the first contact location $P_{Rear}$. In contrast, the second contact location $P_{Front}$ is located on a rear side of the second spring 1278, 1378. Therefore, the second spring 1278, 1378 can only be supported by, that is, receive a load from $P_{Front}$ when the second spring 1278, 1378 is deflected forward and tries to move rearward to return to its resting position. During plantarflexion when the springs are deflected rearward, only the first spring 1268, 1368 is supported by $P_{Rear}$ to provide stiffness to the foot. The second spring 1278, 1378 is not engaged $P_{Front}$ during plantarflexion. During dorsiflexion when the springs are deflected forward, the first spring 1268, 1368 pivots at $P_{Rear}$ and the second spring 1278, 1378 pivots at $P_{Front}$ respectively at to adjust a stiffness to the foot. Therefore, the prosthetic foot 1200, 1300 also has a lower stiffness and/or is softer during plantarflexion (for example, during heel strike) than during dorsiflexion (for example, during toe off).

Figure 13A:
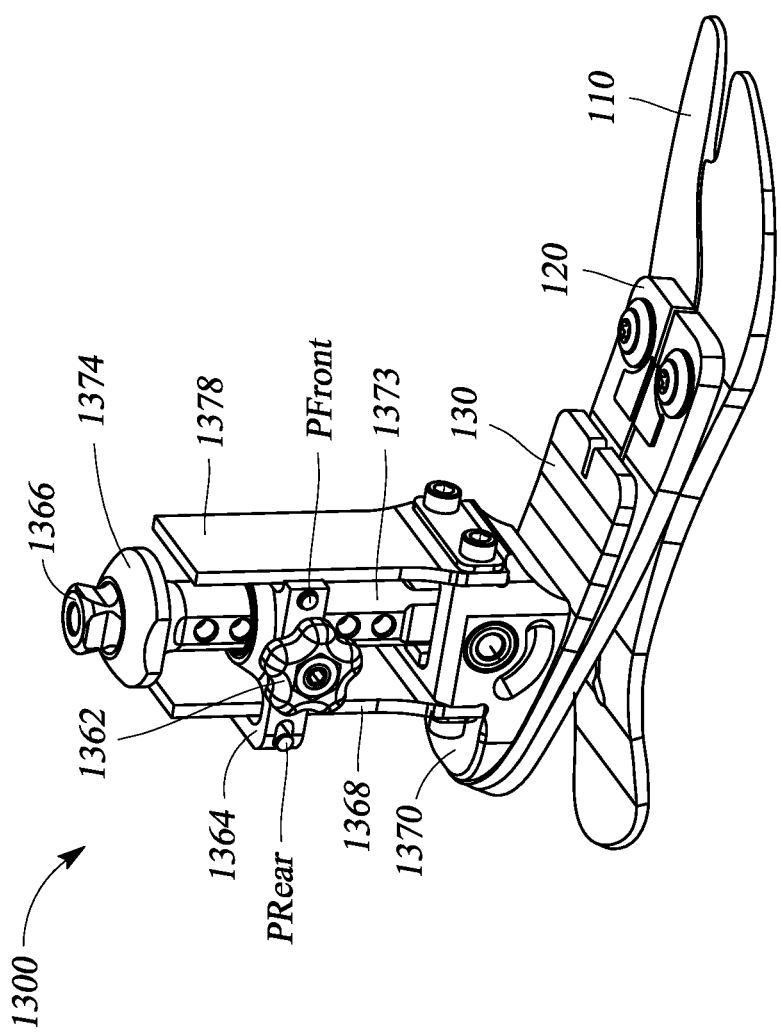
FIG. 13A illustrates a perspective view of a prosthetic foot with another example variable stiffness ankle unit.
Figure 13B:
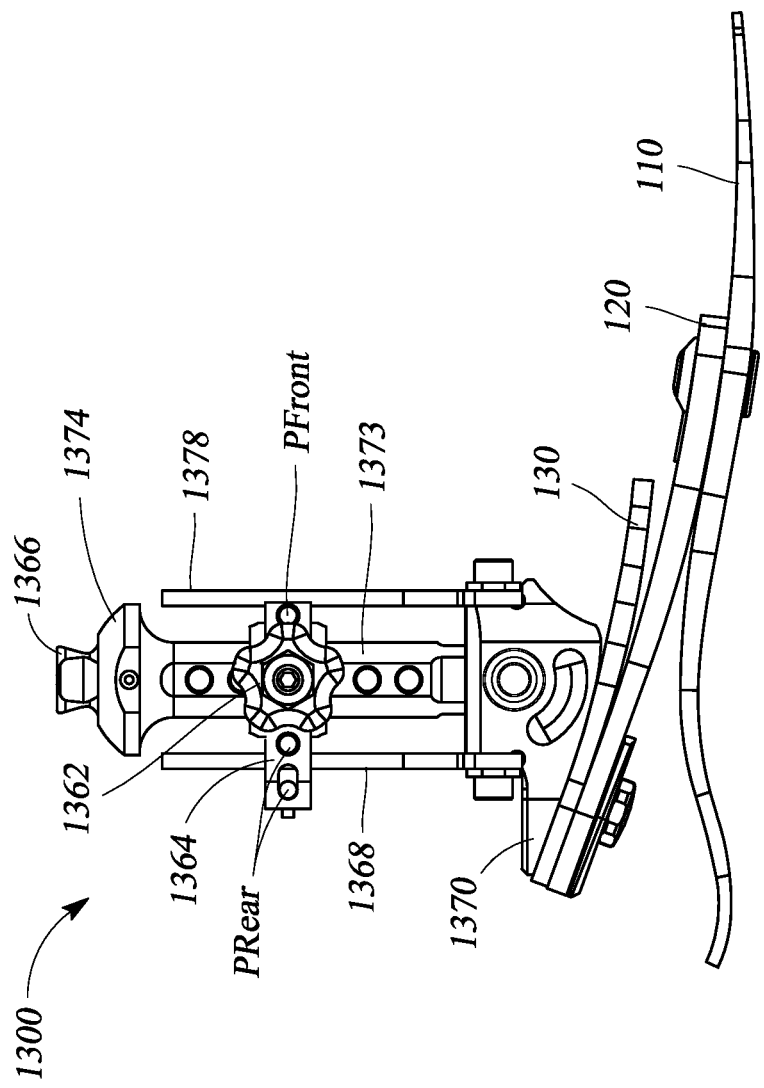
FIG. 13B illustrates a side view of the prosthetic foot of FIG. 13A.
Figure 14A:
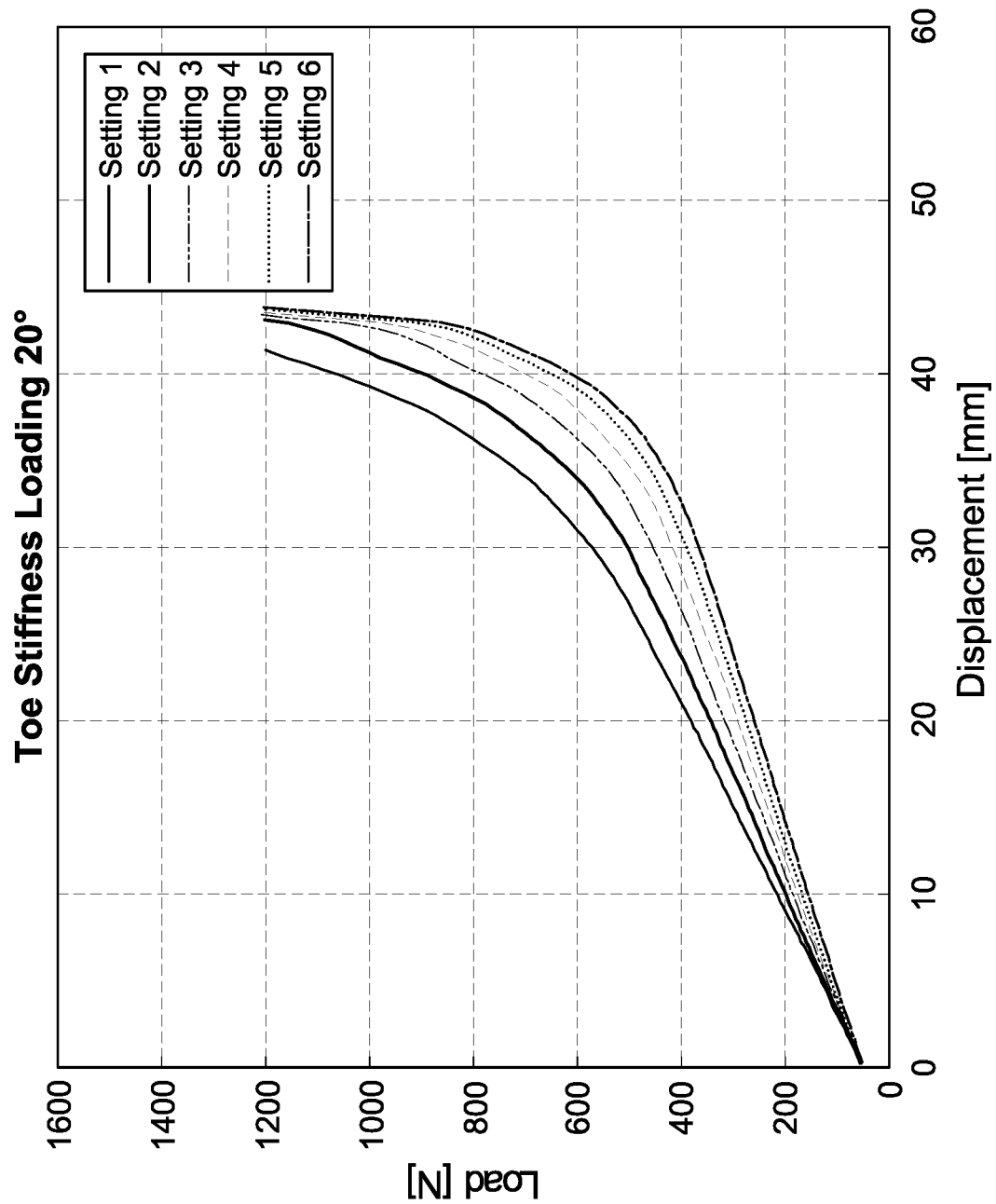
FIGS. 14A and 14B are graphs showing mechanical testing results of example prosthetic feet with a two-spring design.
Figure 14B:
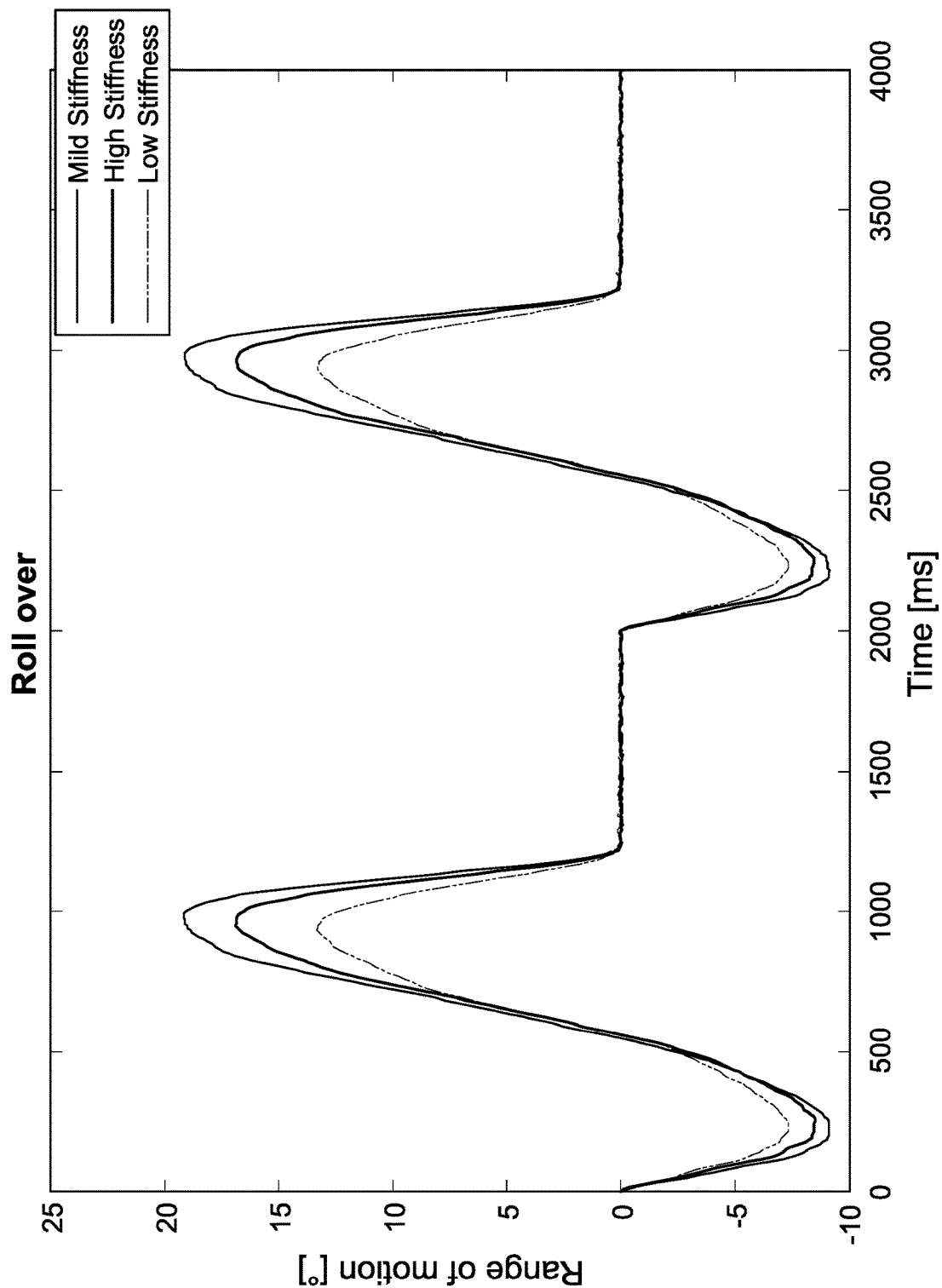

The two-spring design of FIGS. 12A-12B and 13A-13B may provide a greater range of stiffness than the single-spring design. FIG. 14A illustrates results of an example toe-stiffness loading test using a prosthetic foot with the two-spring design. FIG. 14B illustrates a change of range of motion based on different stiffness setting for a prosthetic foot with a two-spring design in the machine-based test setup similar to the set up shown in FIGS. 8B and 8C. The one-spring design of the prosthetic foot 100 described above can reduce noise as well as the size and/or weight of the ankle unit.

In some embodiments, the slider can be moved manually by the user rather than via a motorized actuator. As shown in FIGS. 13A-13B, the slider 1364 can be coupled with a knob 1362. The user can rotate the knob 1362, and the rotation of the knob 1362 can be converted to an axial translation of the slider 1364 along the length of the pylon 1374. For example, rotation of the knob 1362 can decouple the slider 1364 from the pylon 1274 (e.g., withdraw a pin of the knob 1362 from holes on the slider 1274), allowing the user to manually adjust a position of the slider 1364 along the pylon 1274, after which the user can rotate the knob 1362 to lock the new position of the slider 1364 (e.g., by rotating the knob 1362 so a pin associated with the knob 1362 extends into holes in the pylon 1274). The manual control needs not be restricted to the knob 1362, but can be any mechanical features, such as a sliding tab that can be moved along a track on the pylon or the like. In the pylon 1274, 1374 shown in FIGS. 12A-B and 13A-B, a plurality of indentations 1273, 1373 can be included along the length of the pylon 1274, 1374. The indentations 1273, 1373 can provide a visual indication of the position of the slider 1276, 1364. In the examples where the slider is moved manually by the user, one of the indentations may also engage a pin, a screw, or any fastener to maintain the position of the slider at the height of that indentation. The prosthetic foot 100 described above may also replace the motor 162 with a manual stiffness regulating feature disclosed herein.

In some embodiments, the variable stiffness ankle unit can include a single cantilever spring. The spring can be located anterior or posterior to the pylon. The slider of the ankle unit can include a single contact location for the spring. Accordingly, such an ankle unit is configured to change stiffness in either the plantarflexion direction or the dorsiflexion direction.

In some embodiments, the ankle unit (e.g., the ankle unit 160) of the prosthetic foot described herein (e.g., the prosthetic foot 100) can be pivotably coupled to one of the foot members 110, 120, 130 to allow the ankle unit to rotate medially (e.g., towards the inside of the prosthetic foot) or laterally (e.g., towards the outside of the prosthetic foot) in the frontal plane (or coronal plane that divides the body into anterior or posterior portions) about an axis perpendicular to, for example, an axis extending between the heel end 112 and the toe end 114. For example, the ankle unit (e.g., the ankle unit 160) can be rotatably connected to, for example, the upper foot member 130 via a pivot joint (e.g., ball joint, spherical joint).

In some embodiments, the ankle unit (e.g., the ankle unit 160) can include one or more cantilever springs (e.g., the cantilever spring 168) positioned along the sides (e.g., medial side, lateral side) of the ankle unit and engage (e.g., contact) a slider (e.g., the slider 164). The cantilever springs can engage the slider at one or more contact locations (e.g., P1 and P2 as described herein). As describe herein, the contact locations can move up or down along the length of the slider to adjust the stiffness of the cantilever springs. For example, when the contact locations move down towards a base (e.g., the base 170) of the ankle unit, the stiffness of the cantilever spring may increase, making it more difficult for the user of the prosthetic foot to rotate the ankle unit medially or laterally. On the other hand, when the contact locations move up towards a pylon (e.g., the pylon 174) of the ankle unit, the stiffness of the cantilever spring may decrease, making it easier for the user of the prosthetic foot to rotate the ankle unit medially or laterally.

In some embodiments, the ankle unit (e.g., the ankle unit 160) can include one or more cantilever springs (e.g., the cantilever spring 168) and the slider (e.g., the slider 164) on its medial side, lateral side, or both. By having the cantilever springs and the slider on both the medial and the lateral side, the ankle unit can provide separately variable/adjustable stiffness in the medial-lateral direction. Alternatively or additionally, the ankle unit (e.g., the ankle unit 160) can include one or more cantilever springs (e.g., the cantilever spring 168) and the slider (e.g., the slider 164) on its anterior side, posterior side, or both. By having the cantilever springs and the slider on both the posterior and the anterior side, the ankle unit can provide separately variable/adjustable stiffness in the anterior-posterior direction. In some embodiments, the ankle unit can include separate cantilever springs and sliders for its medial, lateral, posterior, and anterior sides. As such, the ankle unit can provide separate anterior/posterior and medial/lateral variable stiffness control.

In some embodiments, the pivot joint between the ankle unit (e.g., the ankle unit 160) and, for example, the upper foot member 130 can have fixed or variable stiffness. In some examples, a user of the prosthetic foot may be able to adjust (e.g., manually) the stiffness of the pivot joint between the base 170 and the upper foot member 130. Additionally or alternatively, the stiffness of the pivot joint between the base 170 and the upper foot member 130 may automatically adjust based on, for example, shifts of the user's body weight.

In some embodiments, the ankle unit (e.g., the ankle unit 160) can have the same or different degree of movement when rotated medially or laterally relative to, for example, the upper foot member 130.

In some embodiments the ankle unit (e.g., the ankle unit 160) may be able to rotate medially or laterally between about 30 degrees and about 120 degrees, between about 40 degrees and about 110 degrees, between about 50 degrees and about 100 degrees, between about 60 degrees and about 90 degrees, between about 70 degrees and about 80 degrees, or about 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, or ranges including any two of the aforementioned values.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

Certain methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

The various illustrative logical blocks, modules, routines, and/or algorithm steps described in connection with the embodiments disclosed herein can be implemented as electronic hardware (e.g., ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic ankle with variable stiffness and configured to couple to a plurality of foot elements, the prosthetic ankle comprising:
   an adapter configured to operably couple to a user's limb;
   a base configured to couple to one or more of the plurality of foot elements;
   a pylon extending between the adapter and the base, wherein the pylon is an elongate beam, the pylon comprising a longitudinal axis and first and second ends along the longitudinal axis, the first end fixedly coupled to a bottom surface of the adapter and the second end rotatably coupled to the base;
   at least one cantilever spring having a first end fixedly coupled to the base and a free second end extending toward the first end of the pylon; and
   a slider configurable to be movable relative to the longitudinal axis of the pylon in response to a user input, the slider including at least one contact location for the at least one cantilever spring, the at least one contact location positioned between the first end and the free second end of the at least one cantilever spring,
   wherein movement of the slider relative to the longitudinal axis of the pylon is configured to vary a position of the at least one contact location so as to vary a stiffness of the prosthetic ankle.

2. The prosthetic ankle of claim 1, further comprising a motor configured to move the slider relative to the longitudinal axis of the pylon.

3. The prosthetic ankle of claim 2, further comprising a processor configured to monitor a position of the slider relative to the longitudinal axis of the pylon.

4. The prosthetic ankle of claim 3, further comprising a wireless transmitter and/or receiver configured to transmit the monitored position to a remote user control device.

5. The prosthetic ankle of claim 4, wherein the processor is configured to receive user instructions input by a user on the remote user control device via the wireless transmitter and/or receiver, the user input comprising the received user instructions, and wherein the processor is configured to adjust the position of the slider based on the received user instructions.

6. The prosthetic ankle of claim 1, further comprising a knob, the user input comprising a user manually manipulating the knob to manually move the slider relative to the longitudinal axis of the pylon.

7. The prosthetic ankle of claim 1, wherein the at least one contact location comprises a first contact location and a second contact location for the at least one cantilever spring, the first and second contact locations spaced apart from each other and positioned between the first end and the free second end of the at least one cantilever spring.

8. The prosthetic ankle of claim 7, wherein the second contact location is closer to the base than the first contact location.

9. The prosthetic ankle of claim 7, wherein the first and second contact locations are on opposite sides of the at least one cantilever spring, the at least one cantilever spring supported by the second contact location when the adapter is rotated about the second end of the pylon away from the at least one cantilever spring, and the at least one cantilever spring supported by the first contact location when the adapter is rotated about the second end of the pylon toward the at least one cantilever spring.

10. The prosthetic ankle of claim 7, wherein the at least one cantilever spring comprises a first cantilever spring and a second cantilever spring on opposite sides of the pylon, the first contact location configured to support the first cantilever spring and the second contact location configured to support the second cantilever spring.

11. The prosthetic ankle of claim 1, wherein the at least one cantilever spring comprises a taper from the second free end toward the first end of the spring.

12. The prosthetic ankle of claim 10, wherein the first and second cantilever springs are supported by the first and second contact locations relatively when the pylon rotates about the second end of the pylon in a first direction, and only the first cantilever spring is supported by the first contact location when the pylon rotates about the second end of the pylon in a second direction opposite the first direction.

13. The prosthetic ankle of claim 1, wherein the at least one cantilever spring extends parallel to the longitudinal axis of the pylon and the free second end of the at least one cantilever spring terminates prior to the first end of the pylon and below the adapter.

14. A prosthetic foot comprising:
a prosthetic ankle comprising:
an adapter configured to operably couple to a user's limb;
a base;
a pylon extending between the adapter and the base, wherein the pylon is an elongate beam, the pylon comprising a longitudinal axis and first and second ends along the longitudinal axis, the first end fixedly coupled to a bottom surface of the adapter and the second end rotatably coupled to the base;
at least one cantilever spring having a first end fixedly coupled to the base and a free second end extending toward the first end of the pylon; and
a slider configurable to be movable relative to the longitudinal axis of the pylon in response to a user input, the slider including a first contact location and a second contact location for the at least one cantilever spring, the first and second contact locations spaced apart from each other and positioned between the first end and the free second end of the at least one cantilever spring;
a lower foot member, the lower foot member comprising a toe end and a heel end; and
an intermediate foot member located between the lower foot member and the prosthetic ankle, the intermediate foot member having a proximal end and a distal end, the base of the prosthetic ankle fixed coupled to the intermediate foot member at or near the proximal end, the lower foot member coupled to the intermediate foot member at or near the distal end,
wherein movement of the slider relative to the longitudinal axis of the pylon is configured to vary positions of the first and second contact locations so as to vary a stiffness of the prosthetic ankle.

15. The prosthetic foot of claim 14, wherein the distal end of the intermediate foot member terminates proximal to the toe end of the lower foot member.

16. The prosthetic foot of claim 14, wherein the intermediate foot member comprises a taper so that a thickness of the intermediate foot member increases from the proximal end to the distal end.

17. The prosthetic foot of claim 14, further comprising an upper foot member located between the intermediate foot member and the base of the prosthetic ankle, the upper foot member having a proximal end and a distal end, the base of the prosthetic ankle fixed coupled to the upper foot member at or near the proximal end of the upper foot member.

18. The prosthetic foot of claim 17, wherein the distal end of the upper foot member is separated from the distal end of the intermediate foot member by a gap when the prosthetic foot is resting on a level surface.

19. The prosthetic foot of claim 14, wherein the at least one cantilever spring is supported by the first contact location when the prosthetic foot is in plantarflexion, and wherein the at least one cantilever spring is supported by the second contact location when the prosthetic foot is in dorsiflexion.

20. The prosthetic foot of claim 19, wherein, for a given location of the slider relative to the longitudinal axis of the pylon, the stiffness of the prosthetic ankle is lower when the prosthetic foot is in plantarflexion than when the prosthetic foot is in dorsiflexion.

21. The prosthetic foot of claim 14, wherein the at least one cantilever spring comprises a first cantilever spring and a second cantilever spring on opposite sides of the pylon, the first contact location configured to support the first cantilever spring and the second contact location configured to support the second cantilever spring.

* * * * *